US012702846B2

(12) United States Patent
Furman et al.

(10) Patent No.: US 12,702,846 B2
(45) Date of Patent: Aug. 11, 2026

(54) ACCESSORY DOCK FOR WIRELESS MEDICAL ACCESSORIES

(71) Applicant: Stryker Corporation, Kalamazoo, MI (US)

(72) Inventors: Aaron Furman, Kalamazoo, MI (US); Scott Batzer, Plainwell, MI (US); Justin McLouth, Kalamazoo, MI (US); Darren Schaaf, Portage, MI (US); Adithya Chandrashekharan, Portage, MI (US); Kerry Castor, Kalamazoo, MI (US); Gwynneth St. John, Kalamazoo, MI (US); Ed Crampton, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 266 days.

(21) Appl. No.: 18/397,171

(22) Filed: Dec. 27, 2023

(65) Prior Publication Data

US 2024/0216705 A1 Jul. 4, 2024

Related U.S. Application Data

(60) Provisional application No. 63/435,779, filed on Dec. 28, 2022.

(51) Int. Cl.
*A61N 1/39* (2006.01)
*G16H 40/67* (2018.01)

(52) U.S. Cl.
CPC ......... *A61N 1/3925* (2013.01); *A61N 1/3904* (2017.08); *A61N 1/3968* (2013.01); *A61N 1/3981* (2013.01); *G16H 40/67* (2018.01)

(58) Field of Classification Search
None
See application file for complete search history.

(56) References Cited

U.S. PATENT DOCUMENTS

2018/0366992 A1 12/2018 Stever
2020/0305805 A1* 10/2020 Freeman .............. A61B 5/0006

OTHER PUBLICATIONS

Extended European Search Report mailed Feb. 14, 2024 for European Application No. 23220632.6, a foreign counterpart to U.S. Appl. No. 18/397,171, 7 pages.

* cited by examiner

*Primary Examiner* — Carl H Layno
*Assistant Examiner* — Bryan McAllister Lee
(74) *Attorney, Agent, or Firm* — Lee & Hayes, P.C.

(57) ABSTRACT

An accessory dock is described, the accessory dock for docking wireless accessories that are configured to be used with a medical device. The accessory dock has at least one docking receptacle configured to receive a wireless accessory. In some examples, the wireless accessory receives power from the medical device upon being positioned within a threshold distance of the medical device to charge a battery of the wireless accessory. In some examples, the wireless accessory pairs with the medical device upon being positioned within a threshold distance of the medical device. In some examples, a processor of the medical device causes performance of an accessory health check upon the wireless accessory being docked in the docking receptacle, the accessory health check for determining a readiness of the wireless accessory.

20 Claims, 8 Drawing Sheets

106
502(1)
502(2)
500(1)
500(2)
108

ACCESSORY DOCK FOR WIRELESS MEDICAL ACCESSORIES

CROSS-REFERENCE TO RELATED APPLICATION

This application claims the benefit of U.S. Provisional Application No. 63/435,779, titled "ACCESSORY DOCK FOR WIRELESS MEDICAL ACCESSORIES" and filed on Dec. 28, 2022, and which is incorporated by reference herein in its entirety.

BACKGROUND

A medical device, such as a monitor-defibrillator, is often used to monitor and treat patients at an emergency scene, and the medical device is typically moved with the patient as the patient is transported along a chain of care from the emergency scene to a medical facility, such as an emergency room at a hospital. When treating a patient, emergency responders receive information regarding the patient from various sources, such as from wired accessories that are plugged into the medical device via respective cables and used to monitor physiological parameters of the patient such as oxygen saturation, electrocardiogram (ECG), and blood pressure, among others. As the number of wired accessories increases, the cables that connect them to the medical device can get tangled and become a nuisance to the emergency responders.

DETAILED DESCRIPTION

Figure 1:
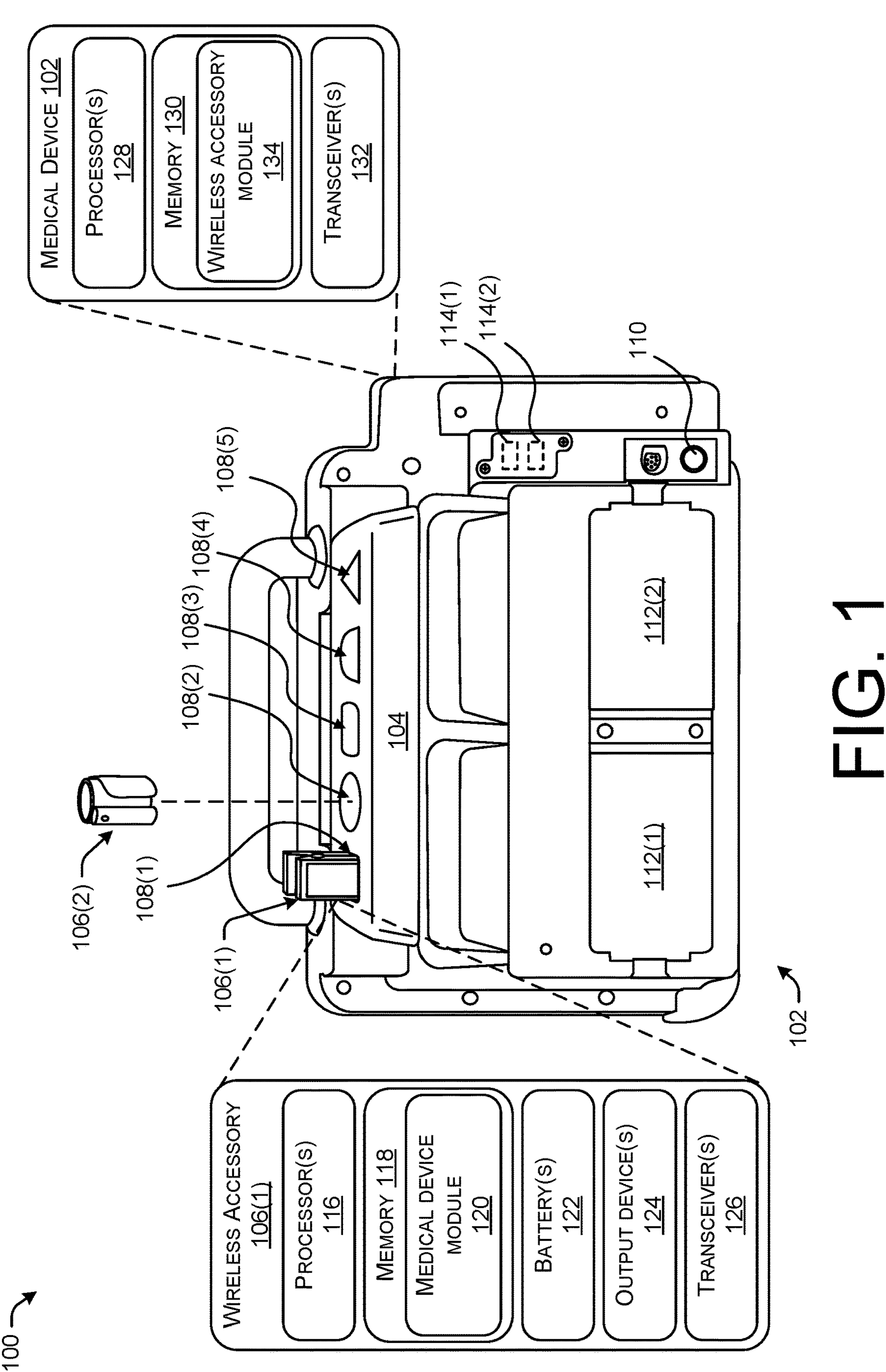
FIG. 1 illustrates an example system including a medical device with an accessory dock and wireless accessories that are usable with the medical device and configured to dock in the accessory dock, according to the techniques described herein.

This disclosure provide an accessory dock for docking wireless accessories that are configured to be used with a medical device. As noted above, medical devices often use wired accessories. For example, wired accessories may be used to collect physiological data regarding a subject (e.g., a patient) who is being monitored and/or treated by the medical device. The system disclosed herein includes wireless accessories that are configured to be used with a medical device, such as a monitor-defibrillator. These wireless accessories do not need a cable to connect to the medical device, and, as a consequence, users of the medical device, such as emergency responders, are not burdened by a nest of tangled cables, which can improve the efficiency and the outcome of patient care. Despite these improvements, wireless accessories require power to operate. For example, the wireless accessories may be powered by one or more on-board batteries, which have limited power and which need to be replaced or recharged periodically. Furthermore, wireless accessories are easier to misplace because there are no cables tethering the accessories to the medical device.

The accessory dock disclosed herein may be part of, or coupled to, a medical device, such as a monitor-defibrillator. Although the examples described herein pertain to a monitor-defibrillator, it is to be appreciated that the disclosed accessory dock is usable across a wide variety of types of medical devices that utilize wireless accessories. Accordingly, this disclosure is not limited to an accessory dock for a monitor-defibrillator. The accessory dock includes one or more docking receptacles configured to receive one or more wireless accessories. Accordingly, the accessory dock functions as a storage mechanism that serves as a convenient place to store one or more wireless accessories when the accessories are not being used. This, in turn, reduces the risk of losing the wireless accessories. The accessory dock also serves as an efficient packing mechanism to make packing and transporting the wireless accessories easier. For example, a user, such as a rescuer at an emergency scene, may monitor and/or treat a subject at the scene using the medical device and a wireless accessory, and when the rescuer is finished providing care to the subject, or when the subject is passed off to another medical device to receive care therefrom, such as when the subject arrives at a hospital, the rescuer can dock the wireless accessory in the accessory dock of the medical device so that the wireless accessory is conveniently transportable with the medical device and/or so that the wireless accessory can be quickly located and retrieved the next time a rescuer uses the wireless accessory with the medical device.

In some examples, the accessory dock is configured to function as an accessory charging station. For example, a wireless accessory may include one or more batteries that power one or more electronic components of the wireless accessory. As an illustrative example, the wireless accessory may be configured to detect an oxygen saturation level of a subject (e.g., a wireless peripheral oxygen saturation ($SpO_2$) sensor), and the on-board battery of such an accessory may power the electronic components (e.g., the sensor circuitry) for detecting the oxygen saturation level of the subject, and the battery may also power other components, such as an input device(s) and/or an output device(s) (e.g., a display), etc. Over time, as the wireless accessory is used, the charge level of the on-board battery may decrease. The disclosed accessory dock may serve as a convenient charging station to charge and/or recharge the battery of this wireless accessory. Such charging may be performed wirelessly and/or via a charging connector. Accordingly, upon positioning the wireless accessory within a threshold distance of the medical device with the accessory dock, the wireless accessory may receive power from the medical device to charge or recharge the battery. For example, the battery of the wireless accessory may begin charging or recharging wirelessly in response to the accessory being brought within a wireless charging range/distance of the medical device. In some examples, the wireless accessory is within the wireless charging range/distance when the accessory is docked in a designated docking receptacle of the accessory dock. In some examples, the battery of the wireless accessory may begin charging or recharging when the accessory is docked in a designated docking receptacle and thereby connected to a physical charging connector, such as a universal serial bus (USB) connector. In these examples, the user does not have to perform additional actions for charging the wireless accessory (e.g., the user does not have to remember to charge the accessory) if the accessory dock is used to store the wireless accessory when it is not in use. For instance, when a user is finished using the wireless accessory to monitor and/or treat a patient in conjunction with the medical device, the user can place the wireless accessory in a designated docking receptacle of the accessory dock, and the battery of the accessory is charged automatically (e.g., without user intervention), and the next user who undocks the wireless accessory will find that the charge level of the battery of the wireless accessory is full, or at least recharged to a level that is higher than the charge level of the battery at a time when the accessory was docked.

In some examples, the accessory dock is configured to function as an accessory pairing mechanism. For example, a wireless accessory may include a transceiver for communicating wirelessly with the medical device. In these examples, upon positioning the wireless accessory within a threshold distance of the medical device with the accessory dock, the wireless accessory may pair with the medical device so that the wireless accessory can communicate with the correct medical device. Pairing the wireless accessory with a particular medical device prevents data (e.g., sensitive patient data) from being transmitted to the wrong medical device. This not only preserves privacy for the patient, but it ensures that the patient is provided quality care, such as during an emergency, because the medical device may use the data collected by the wireless accessory to perform one or more functions, such as for administering defibrillation therapy (e.g., an electrical shock) to a subject. In some examples, the wireless accessory is within the pairing range/distance of the medical device when the accessory is docked in a designated docking receptacle of the accessory dock. Accordingly, the user does not have to perform additional actions in order to pair the wireless accessory (e.g., the user does not have to perform explicit pairing actions other than placing the wireless accessory in a designated docking receptacle). For instance, when a user purchases a new wireless accessory for use with a medical device, the user can place the wireless accessory in a designated docking receptacle of the accessory dock, and the wireless accessory can exchange pairing information (e.g., near-field communication (NFC) information, BLUETOOTH® information, etc.) with the medical device to automatically (e.g., without user intervention) pair with the medical device. When the user, or a different user, subsequently undocks the wireless accessory, the wireless accessory can use the pairing information to communicate wirelessly with the medical device from farther distances therefrom.

In an example scenario, a subject may be experiencing sudden cardiac arrest, and a bystander may have called emergency services to help the subject. A crew of emergency medical technicians (EMTs) may arrive at the scene in an ambulance, and an EMT may carry a monitor-defibrillator with one or more wireless accessories docked in the accessory dock to the subject. The EMT may undock a wireless $SpO_2$ sensor from the accessory dock and attach the $SpO_2$ sensor to the subject to detect an oxygen saturation level of the subject. The EMT may also attach a wireless ECG detector to the subject to detect the ECG of the subject, and/or a wireless non-invasive blood pressure (NIBP) sensor to detect a blood pressure of the subject. The EMT may treat the subject with the monitor-defibrillator by administering defibrillation therapy (e.g., one or more electrical shocks) to the subject while physiological parameter data is being collected by the wireless accessories and while the data is being sent wirelessly to the monitor-defibrillator. The subject may be transported in the ambulance to a hospital while the monitor-defibrillator and wireless accessories are used to continue monitoring and treating the subject. After arriving at the hospital, the EMTs may detach the wireless accessories as the subject is received by emergency care personnel at the hospital. An EMT can then store the wireless accessories in the accessory dock of the monitor-defibrillator, and the respective batteries of the wireless accessories may begin recharging and may continue to charge while docked in the accessory dock. In combination with the automatic pairing when the wireless accessories were initially docked in the accessory dock, the features and functionality of the accessory dock disclosed herein reduces the number of steps a user has to perform in order to use the wireless accessories. For example, the EMTs in the scenario described are not concerned with losing the wireless accessories because they are safely and securely stored in the accessory dock, and the EMTs are not concerned with pairing the wireless accessories because they are automatically paired with the medical device, and the EMTs are not concerned with the wireless accessories having enough power to operate during the emergency care because the respective batteries of the accessories charge or recharge while docked in the accessory dock. These and other technical benefits are readily appreciated in light of this disclosure, with detailed reference to the figures provided below.

FIG. 1 illustrates an example system 100 including a medical device 102 with an accessory dock 104 and wireless accessories 106(1) and 106(2) (collectively 106) that are usable with the medical device 102 and configured to dock in the accessory dock 104, according to the techniques described herein. In some examples, the medical device 102 represents a monitor-defibrillator (sometimes referred to herein as an "external defibrillator") configured to administer defibrillation therapy to a subject (e.g., a patient) and to monitor one or more physiological parameters associated with the subject. In some examples, the medical device 102 an automated external defibrillator (AED). It is to be appreciated, however, that the medical device 102 may be any suitable type of medical device that is used with one or more wireless accessories, such as a cardiopulmonary resuscitation (CPR) device (e.g., a mechanical chest compression device), a laryngoscope, an ECG monitor, an ultrasound device, or any other suitable type of medical device.

The wireless accessories 106 may include, without limitation, a wireless $SpO_2$ sensor (e.g., the first wireless accessory 106(1) may represent such a wireless $SpO_2$ sensor) configured to detect an oxygen saturation level of a subject, a wireless NIBP sensor (e.g., the second wireless accessory 106(2) may represent such a wireless NIBP sensor) configured to detect a blood pressure of the subject, a wireless ECG detector configured to detect an ECG of the subject, a wireless airway monitoring device configured to detect a carbon dioxide ($CO_2$) parameter (e.g., end-tidal $CO_2$ ($EtCO_2$)) and/or an airflow parameter and/or a pressure parameter associated with an airway of the subject, a wireless CPR coaching device configured to output coaching information (e.g., timing information for administering chest compressions and/or a ventilation to the subject), or any other suitable type of wireless accessory.

The accessory dock 104 may include one or more docking receptacles 108 (e.g., slots, compartments, ports, etc.), each docking receptacle 108 being configured to receive an individual wireless accessory 106. The example of FIG. 1 shows the accessory dock 104 as having a one-dimensional (1D) array (e.g., a row, a bank, etc.) of docking receptacles 108(1), 108(2), 108(3), 108(4), and 108(5) (collectively 108). Although five docking receptacles 108 are shown in the example of FIG. 1, it is to be appreciated that the accessory dock 104 may include any number of docking receptacles 108, such as a single docking receptacle 108, less than five docking receptacles 108, or more than five docking receptacles. In some examples, the docking receptacles 108 may be of a uniform shape (e.g., the docking receptacles 108 are all the same shape). Accordingly, the accessory dock 108 may be a universal accessory dock 104 that is configured to receive any wireless accessory 106 in any of the docking receptacles 108. In the example of FIG. 1, the docking receptacles 108 have different shapes. In some examples, each docking receptacle 108 may have a shape that is unique amongst the set of docking receptacles 108 of the accessory dock 104. For example, the first docking receptacle 108(1) has a first shape (e.g., a square shape), the second docking receptacle 108(2) has a second shape (e.g., a circular shape), the third docking receptacle 108(3) has a third shape (e.g., an elliptical shape), the fourth docking receptacle 108(4) has a fourth shape (e.g., a semi-circular shape), and the fifth docking receptacle 108(5) has a fifth shape (e.g., a triangular shape), and these shapes are different shapes. The shapes of the docking receptacles 108 may indicate, to a user, which docking receptacle 108 is designated for a particular wireless accessory 106. For example, the shape of the first docking receptacle 108(1) may match a shape of a first housing of the first wireless accessory 106(1). In this manner, a user can compare the shape of the housing of the first wireless accessory 106(1) to the shapes of the docking receptacles 108(1)-(5) to identify the correct/designated docking receptacle 108(1) that is configured to receive the first wireless accessory 106(1). In some examples, additional indicia may be provided in association with the docking receptacles 108 to inform the user as to where the wireless accessories 106 are to be docked in the accessory dock 104, such as color coding next to each docking receptacle 108 and/or text (e.g., "$SpO_2$" next to the first docking receptacle 108(1), "NIBP" next to the second docking receptacle 108(2), etc.). In some examples, the most-frequently-used accessory 106 is configured to be docked in the most accessible docking receptacle 108 (e.g., in the far left docking receptacle 108(1), the far right docking receptacle 108(5), at the front, the top, or another conveniently accessed location on the accessory dock 104).

In some examples, the accessory dock 104 is part of (e.g., integrally formed) with the medical device 102. For example, during manufacture of the medical device 102, the accessory dock 104 may be mounted thereto, and, in this example, a consumer who purchases the medical device 102 from a vendor may receive the medical device 102 with the accessory dock 104 integrated therewith. In other words, the accessory dock 104 may be permanently coupled to the medical device 102, in some examples. In other examples, the accessory dock 104 is removably coupled to the medical device 102, such as via a sliding engagement, a clip(s), a fastener (e.g., screws, bolts, etc.). In some examples, the accessory dock 104 is sold separately as an aftermarket accessory for the medical device 102 that converts the medical device 102 into a medical device 102 with a docking station for the wireless accessories 106. As used herein, the term "couple" may refer to an indirect coupling or a direct coupling between elements. The term "couple," as used herein, may also refer to a removable coupling or a permanent coupling between the elements. Elements are permanently coupled if a user or another entity is unable to decouple the elements without destroying or significantly damaging the elements, or without undue effort to disassemble the elements using tools or machinery. Elements are removably coupled if a user or another entity is able to decouple the elements. As used herein, the term "couple" can be interpreted as connect, attach, join, engage, interface, link, fasten, or bind. Unless otherwise specified herein, the term "couple" is to be interpreted as coupling elements in a mechanical sense. Nevertheless, it is to be appreciated that a mechanical coupling of elements may result in an electrical coupling(s) between multiple elements of the system.

FIG. 1 depicts an example accessory dock 104 that is integrally formed with the medical device 102 and is made of a rigid, or semi-rigid material, such as molded plastic with the docking receptacles 108(1)-(5) formed by injection molding the accessory dock 104, for example. It is to be appreciated, however, that the accessory dock 104 may be manufactured in other ways, such as by machining material to form the accessory dock 104, by an additive-manufacturing process (e.g., three-dimensional (3D) printing), or any other suitable method of manufacture. A benefit of the accessory dock 104 being an integral part of, or removably coupled to, the medical device 104 is that the accessory dock 104 stays with the medical device 102, and the user does not have to keep track of a separate accessory dock 104. Nevertheless, the accessory dock 104 may be a separate from the medical device 102, in some examples, such as by attaching the accessory dock 104 to the medical device 102 via a cable. In some examples, the accessory dock 104 may be in the form of a storage bag(s) mounted to the medical device 102. For example, storage bags mounted to the sides of the medical device 102 may include docking receptacles 108 in the form of compartments of the storage bag(s) that the user can open (e.g., unzip) to access the compartments and store wireless accessories 106 therein. An advantage of the accessory dock 104 shown in FIG. 1, as compared to a storage bag serving as the accessory dock is that it may be easier to locate a desired wireless accessory 106 quickly with the implementation of FIG. 1. In some examples, a storage bag may include an accessory dock 104 like the one shown in FIG. 1 within a compartment of the storage bag, and the user may open (e.g., unzip) the compartment to access the accessory dock 104. This may serve as an extra "layer" of protection if, say, a wireless accessory 106 were to fall out of a docking receptacle 108 during transport because the accessory 106 would remain in the compartment of the storage bag. Such an implementation may also protect the wireless accessories 106 from environmental elements (e.g., rain, dirt, etc.). In some examples, the accessory dock 104 may have a cover or a similar protective element to protect the wireless accessories 106 from damage and/or from falling out of the accessory dock 104. In this example, a user may lift a cover of the accessory dock 104 to expose the wireless accessories 106.

The medical device 102 can include one or more power sources and/or components for accessing external power sources. For example, the medical device 102 may include a power connector 110 configured to receive a power cable for connecting the medical device 102 to an external source of power (e.g., a power outlet with access to mains electricity, or grid power). Additionally, or alternatively, the medical device 102 may further include one or more batteries 112. FIG. 1 shows an example where the medical device 102 includes multiple batteries 112 including a first battery 112(1) and a second battery 112(2). This redundancy of on-board power for the medical device 102 may be beneficial in emergency scenarios, such as when the first battery 112(1) runs out of charge, the second battery 112(2) can be used as a backup for powering the electronic components of the medical device 102. In general, access to these sources of power can provide power to the various electronic components of the medical device 102 to carry out the functions of the medical device 102, such as monitoring and/or treating a subject.

The accessory dock 104 may be configured to access one or more of the power sources accessible to the medical device 102. For example, the accessory dock 104 may be coupled to a physical connector of the medical device 102, and the accessory dock 104 may receive power through such a physical connector, such as power provided by the battery 112(1), the battery 112(2), or power originating from mains electricity, if the medical device 102 is plugged in via the power connector 110. In some examples, both power and data may be passed to the accessory dock 104 via the physical connector. In some examples, the accessory dock 104 is mechanically coupled to the medical device 102, but power and/or data is received by the accessory dock 104 from the medical device 102 wirelessly. In either implementation, the accessory dock 104 may receive power from the power source(s) accessible to the medical device 102, and the accessory dock 104 may exchange data or otherwise communicate with the medical device 102.

In some examples, the accessory dock 104 is coupled to one or more external ports 114(1), 114(2) (e.g., USB ports) to receive power and/or data from the medical device 102. For example, as discussed above, the accessory dock 104 may be an aftermarket product that a user purchases and mounts to the medical device 102, and one or more cables may be connected to the accessory dock 104 and to the external port(s) 114(1), 114(2) of the medical device 102 to configure the accessory dock 104 for receiving power and/or exchanging data with the medical device 102. In some examples, the accessory dock 104 includes its own on-board power source, such as a battery, and/or the accessory dock 104 includes a power connector to connect the accessory dock 104 to mains electricity (e.g., via a power outlet). In examples where the accessory dock 104 includes its own on-board battery, the battery may be rechargeable, and such recharging may occur, for example, when the medical device 102 is plugged in via the power connector 110.

As mentioned above, the accessory dock 104 functions as a storage mechanism that serves as a convenient place to store one or more wireless accessories 106 when the accessories 106 are not being used. In some examples, the accessory dock 104 is configured to function as an accessory charging station such that the respective batteries of the wireless accessories 106 charge or recharge in response to positioning the wireless accessories 106 within a threshold distance of the medical device 102 and/or the accessory dock 104, such as by docking the accessories 106 in a designated docking receptacle 108. In some examples, the accessory dock 104 is configured to function as an accessory pairing mechanism, such that the wireless accessories 106 pair with the medical device 102 in response to positioning the wireless accessories 106 within a threshold distance of the medical device 102 and/or the accessory dock 104, such as by docking the accessories 106 in a designated docking receptacle 108. In some examples, the accessory dock 104 functions in other ways, such as a hub for enabling data to be sent/received to/from a remote computing system, as a tether for keeping track of wireless accessories 106 (e.g., tracking location and/or distance of the accessories 106 relative to the medical device 102 and/or the accessory dock 104), and/or as a readiness management mechanism that performs accessory health checks on the wireless accessories 106 to ensure that they are ready to be used with the medical device 102. These and other functions are described in more detail below with respect to the following figures.

FIG. 1 illustrates example components of the first wireless accessory 106(1), which may be representative of the components of any wireless accessory 106 that is usable with the medical device 102. For example, the wireless accessory 106 may include a processor(s) 116, such as a central processing unit (CPU), a graphics processing unit (GPU), both CPU and GPU, or another processing unit or component known in the art. The processor(s) 116 is operably connected to memory 118. In various implementations, the memory 118 is volatile (such as random access memory (RAM)), non-volatile (such as read only memory (ROM), flash memory, etc.) or some combination of the two. The memory 118 stores instructions that, when executed by the processor(s) 116, cause the processor(s) 116 to perform various operations described herein. In various examples, the memory 118 stores methods, threads, processes, applications, objects, modules, any other sort of executable instruction, or a combination thereof. An examples depicted in FIG. 1 includes a medical device module 120 that configures the wireless accessory 106 to interoperate with the medical device 102, such as by facilitating the exchange of pairing information with the medical device 102, enabling or disabling charging of a battery 122 using a power source(s) accessible to the medical device 102, and/or other functionalities described herein. As used herein, the term "module," and its equivalents, refers to data including instructions that, when executed by one or more processors, cause the processor(s) to perform one or more operations. In some cases, the memory 118 stores files, databases, or a combination thereof. For example, the wireless accessory 106 may collect data (e.g., physiological parameter data) during use of the wireless accessory 106, and this and other data may be stored, at least temporarily, in the memory 118.

In some examples, the memory 118 includes RAM, ROM, electrically erasable programmable read-only memory (EEPROM), flash memory, or any other memory technology. In some examples, the memory 118 includes CD-ROMs, digital versatile discs (DVDs), content-addressable memory (CAM), and/or other optical storage, magnetic cassettes, magnetic tape, magnetic disk storage and/or other magnetic storage devices, and/or any other medium (e.g., non-transitory computer-readable medium) which can be used to store the desired information and which can be accessed by the processor(s) 116.

The wireless accessory 106 may further include a power source(s), such as a battery(ies) 122. The battery(ies) 122 can provide power to the various electronic components of the wireless accessory 106. In some examples, the wireless accessory 106 is configured to be placed into a sleep state when it is not in use, which may conserve power. In these examples, the wireless accessory 106 may "wake up" in response to any suitable trigger, and, in response, the battery(ies) 122 may supply power to an electronic component(s) of the wireless accessory 106. A user may provide user input to wake up the wireless accessory 106 (e.g., by touching a touch-sensitive display), or the wireless accessory 106 may wake up based on a sensor (e.g., an ambient light sensor, an accelerometer, etc.) sensing a state change. Although FIG. 1 depicts the wireless accessory 106 as including a battery(ies) 122, it is to be appreciated that the wireless accessory 106 can be battery-less and configured to harvest energy from an ambient energy source, such as from sunlight (e.g., a solar/photovoltaic cell(s)), from radio waves (e.g., power signals transmitted over radio frequencies (RF) from the medical device 102), thermal energy sources, such as a user/subject wearing the wireless accessory 106, and/or kinetic energy sources, such as a movable mass within the wireless accessory 106. Furthermore, the battery(ies) 122 may be single use or reusable (e.g., rechargeable).

The wireless accessory 106 may further include one or more output devices 124, such as a display(s), a light emitting element(s) (e.g., a light emitting diode(s) (LED(s))), an electrochromic material(s), a speaker(s), a haptic actuator(s), or the like. In some examples, the wireless accessory 106 may further include a transceiver 126 (e.g., a wireless radio, antenna, or the like) for communicating wirelessly with the medical device 102 and/or with other devices, such as with other ones of the wireless accessories 106. The transceiver(s) 126 may include any sort of wireless transceivers capable of engaging in wireless communication (e.g., RF communication), such as WI-FI®, WIGIG®, WIMAX®, BLUETOOTH®, NFC, radio frequency identification (RFID), or infrared communication.

Turning to the components of the medial device 102, FIG. 1 shows that the medical device 102 includes a processor(s) 128, memory 130, and a transceiver(s) 132. These components may be the same as or similar to the processor(s) 116, the memory 118, and the transceiver(s) 126, respectively, as described above with respect to the wireless accessory 106. In some examples, the corresponding components of the medical device 102 may be higher-performance components with more computing capacity, as compared to similar components of the wireless accessory 106. The memory 130 stores instructions that, when executed by the processor(s) 128, cause the processor(s) 128 to perform various operations described herein. In various examples, the memory 130 stores methods, threads, processes, applications, objects, modules, any other sort of executable instruction, or a combination thereof. An examples depicted in FIG. 1 includes a wireless accessory module 134 that configures the medical device 102 to interoperate with the wireless accessories 106, such as by facilitating the exchange of pairing information with individual wireless accessories 106, enabling or disabling charging of respective batteries 122 of the wireless accessories 106, and/or other functionalities described herein.

FIG. 1 shows that a first wireless accessory 106(1) is docked in a first docking receptacle 108(1) of the accessory dock 104, and that a second wireless accessory 106(2) is undocked but configured to be docked in the second docking receptacle 108(2). Additional wireless accessories 106 (not shown in FIG. 1) may be configured to be docked in the remaining docking receptacles 108(3)-(5). Consider an example where a user has just docked the first wireless accessory 106(1) in the first docking receptacle 108(1). Upon the first wireless accessory 106(1) being docked in the first docking receptacle 108(1), the first wireless accessory 106(1) may receive power from the medical device 102, such as power originating from the first battery 112(1), the second battery 112(2), and/or from mains electricity and received via the power connector 110, among other possible sources of power.

Figure 2A:
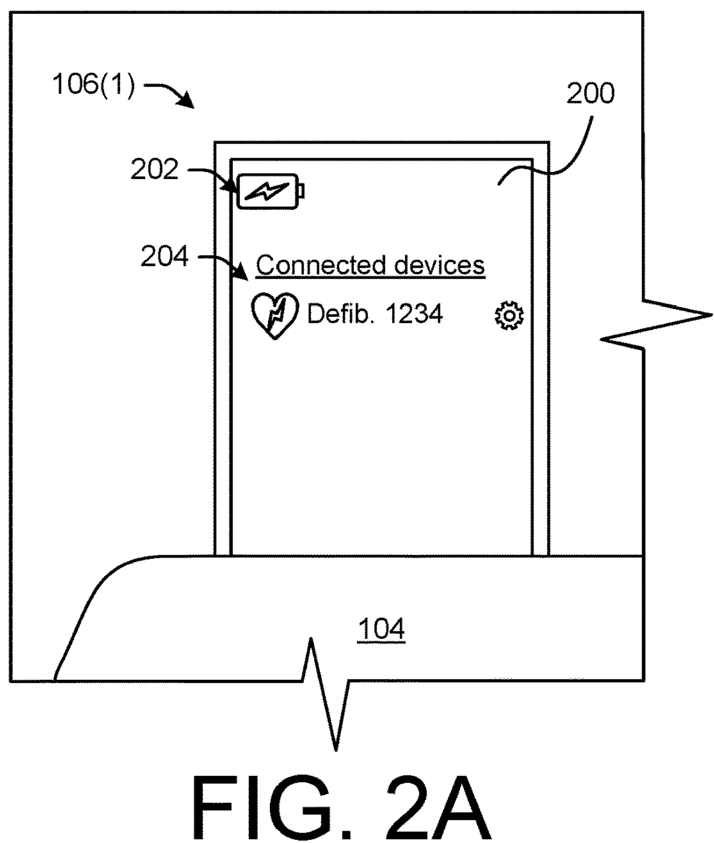
FIG. 2A illustrates an example wireless accessory docked in an accessory dock of a medical device, and an output device of the wireless accessory outputting visual indications that the battery of the wireless accessory is charging and that the wireless accessory is communicatively connected to the medical device, according to the techniques described herein.

FIG. 2A illustrates the first wireless accessory 106(1) docked in the accessory dock 104 of the medical device 102. As shown in FIG. 2A, an output device 124 of the accessory 106(1) in the form of a display 200 is configured to output a visual indication 202 that the battery 122 of the accessory 106(1) is recharging. This visual indication 202 may be output upon the wireless accessory 106(1) being docked in the first docking receptacle 108(1) and upon the accessory 106(1) receiving power from the medical device 102. In a wired charging implementation, the housing of the wireless accessory 106(1) may include a power connector (e.g., a USB connector) on a side of the housing that faces a bottom of the docking receptacle 108(1), for example, and a bottom of the docking receptacle 108(1) may include a corresponding power connector (e.g., a USB connector) that is configured to engage the power connector of the wireless accessory 106(1), and the engagement of these power connectors may initiate charging of the battery 122. In a wireless charging implementation, the charging may be implemented in various ways, such as via radio charging, inductive charging (or near field charging), magnetic resonance charging, and/or electric field coupling. In an illustrative example, the wireless accessory 106(1) may include a first induction coil for recharging the battery 122 in response to magnetic flux generated by a second induction coil of the medical device 102. For example, the second induction coil may be housed in the accessory dock 104 at a location of the docking receptacle 108(1) such that upon the wireless accessory 106(1) being positioned within a threshold distance of the medical device 102, and specifically the second induction coil, the accessory 106(1) may receive power wirelessly via the first induction coil of the accessory 106(1) to recharge the battery 122. It is to be appreciated that the wireless charging range/distance may vary by implementation. In one example, the wireless charging range/distance may be controlled such that the accessory 106(1) does not start receiving power to recharge the battery 122 until the accessory 106(1) is docked in the designated docking receptacle 108(1). In another example, the threshold distance for wireless charging may be greater, and, as such, the accessory 106(1) may begin receiving power as soon as the accessory 106(1) is within a threshold distance of the medical device 102 (e.g., the second induction coil thereof), such as within inches of the medical device 102 housing and/or the second induction coil. Therefore, in some examples, the user may set the wireless accessory 106(1) close to the medical device 102 and/or the user may set the accessory 106(1) on or next to the accessory dock 104 and the wireless accessory 106(1) may still be within range to recharge the battery 122, even in an undocked state.

FIG. 2A further shows that the display 200 is configured to output a visual indication 204 that the wireless accessory 106(1) has been paired with (or is connected to) the medical device 102. This, like the recharging of the battery, may occur upon the accessory 106(1) being positioned within a threshold distance of the medical device 102, which may be the same threshold distance for wireless charging to be initiated, or a different threshold distance. For example, both recharging of the battery 122 and pairing with the medical device 102 may occur automatically (e.g., without user intervention) upon the wireless accessory 106(1) being docked in the first docking receptacle 108(1). Pairing can be implemented using any suitable technology, such as NFC, a passive tag (e.g., a passive RFID tag), infrared, BLUETOOTH®, or even a physical connector to exchange pairing information, etc. In an illustrative example, the wireless accessory 106(1) pairs with the medical device 102 based on a first NFC chip of the wireless accessory 106(1) being positioned within the threshold distance of a second NFC chip of the medical device 102, such as a second NFC chip housed in the accessory dock 104 at a location of the docking receptacle 108(1). In this example, the threshold distance may be satisfied when the wireless accessory 106(1) is docked in the docking receptacle 108(1), and/or when the accessory 106(1) is slightly farther away from the medical device 102, yet still within pairing range/distance thereof. In another example, the wireless accessory 106(1) pairs with the medical device 102 based on a passive RFID tag of the wireless accessory 106(1) being detected by a RFID reader of the medical device 102.

In some examples, the medical device 102 and the wireless accessory 106(1) exchange pairing information when the accessory 106(1) is brought within a threshold distance of the medical device 102, and this pairing information is usable by the medical device 102 and the wireless accessory 106(1) to communicate wirelessly after the wireless accessory 106(1) is undocked and/or after the wireless accessory 106(1) moves farther away from the medical device 102. For example, the devices 102, 106(1) may exchange BLUETOOTH® pairing information upon the wireless accessory 106(1) being docked in the docking receptacle 108(1) for a first time. In this manner, when the accessory 106(1) is undocked and moved farther away from the paired medical device 102, the accessory 106(1) knows that it should be talking to a particular medical device 102, and the medical device 102 knows that it should be talking to a particular accessory 106(1). Accordingly, the pairing ensures that the wireless accessory 106(1) communicates wirelessly with the correct medical device 102, and that data (e.g., sensitive patient data) is sent to the correct medical device 102. In other words, the pairing of the wireless accessory 106(1) with the medical device 102 provides a definitive and secure affirmation of the accessory 106(1) being paired with a medical device 102 with which it should communicate.

In some examples, additional arbitration techniques may be performed to ensure that the accessory 106(1) is paired with the correct medical device 102. For example, signal strength measurements can be made between the wireless accessory 106(1) and multiple devices (e.g., medical devices) in the environment of the wireless accessory 106(1), and the signal strength measurements may be utilized to confirm that the wireless accessory 106(1) is paired with the correct medical device 102 (e.g., the medical device 102 associated with the strongest/greatest signal strength measurement. Otherwise, if the wireless accessory 106(1) measures a strongest/greatest signal strength with an unknown medical device, the accessory 106(1) and/or the correct medical device 102 may output a notification to inform the user of the potential misconfiguration.

In some examples, the pairing of the wireless accessory 106(1) with the medical device 102 may involve performing a series of checks before affirming that the devices 106(1), 102 are paired. For example, the medical device 102 may confirm that the wireless accessory 106 possesses a security key (e.g., a password), and/or the devices 106(1), 102 may check compatibility information (e.g., whether the medical device 102 is one of multiple predefined models, and/or whether the wireless accessory 106 is one of multiple predefined accessory models, etc.). In some examples, the pairing may involve user action, such as the user tapping the accessory 106(1) to the medical device 102 and/or the accessory dock 104 (e.g., a "tap-to-pair" implementation), and/or the user may confirm the pairing by selecting an icon via a button, touch screen, etc. of the medical device 102 and/or a button, touchscreen, etc. of the accessory 106(1).

Figure 2B:
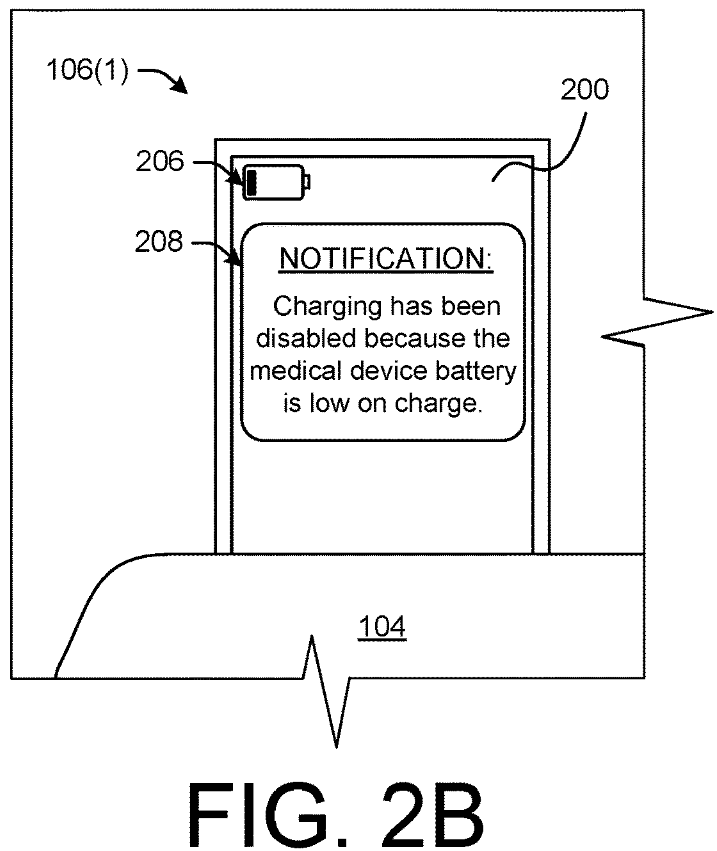
FIG. 2B illustrates an example wireless accessory docked in an accessory dock of a medical device, and an output device of the wireless accessory outputting a visual indication(s) that wireless accessory charging has been disabled, according to the techniques described herein.

FIG. 2B illustrates the wireless accessory 106(1) docked in the accessory dock 104 of the medical device 102. However, in the example of FIG. 2B, the display 200 is outputting visual indications 206, 208 that wireless accessory charging has been disabled, according to the techniques described herein. Wireless accessory charging may be disabled for various reasons. In the example of FIG. 2B, the visual indication 208 informs a user that wireless accessory charging has been disabled because the charge level of the battery 112 of the medical device 102 is too low. For example, since the medical device 102 may save a person's life when used, the medical device 102 may be configured to prioritize reserving battery power for performing a primary/core function of the medical device, such as administering defibrillation therapy, as one example. Accordingly, the processor(s) 128 of the medical device 102 may be configured to execute instructions (e.g., the wireless accessory module 134) stored in memory 130 to determine a charge level of the battery 112(1) and/or 112(2), and to disable wireless accessory charging if the charge level fails to satisfy a threshold charge level. In this scenario, the wireless accessory 106(1) may be prevented from receiving power from the battery 112(1) and/or 112(2) of the medical device 102 so that the medical device 102 mitigates the risk of being unable to perform its primary function (e.g., administering defibrillation therapy) in a safe and effective manner. The visual indication 208 (e.g., notification) output via the display 200 of the wireless accessory 106(1) may inform the user so that the user can take action (e.g., replace and/or recharge the battery 112(1) and/or 112(2) of the medical device 102) to allow for recharging the accessory 106(1) sooner. Thus, even if the wireless accessory 106(1) is docked in the accessory dock 104 or is otherwise brought within wireless charging range/distance of the medical device 102, the wireless accessory 106(1) may be prevented from recharging its own battery 122 in instances where the medical device 102 does not have enough power to charge the accessory 106(1).

Although the example visual indications 202-208 are shown as being output via a display 200 of the wireless accessory 106(1), it is to be appreciated that the wireless accessory 106 may output indications via other types of output devices 124 thereof, such as by illuminating a light emitting element (e.g., a LED) and/or illuminating the light emitting element with a particular color (e.g., red, green, etc.), by outputting a text-to-speech message via a speaker(s) of the accessory 106(1), or the like. It is also to be appreciated that similar indications can be output via the medical device 102, such as via a display of the medical device 102. It is also to be appreciated that the examples described herein with respect to the first wireless accessory 106(1) are equally applicable to the other wireless accessories 106 described herein, such as the second wireless accessory 106(2).

Figure 3:
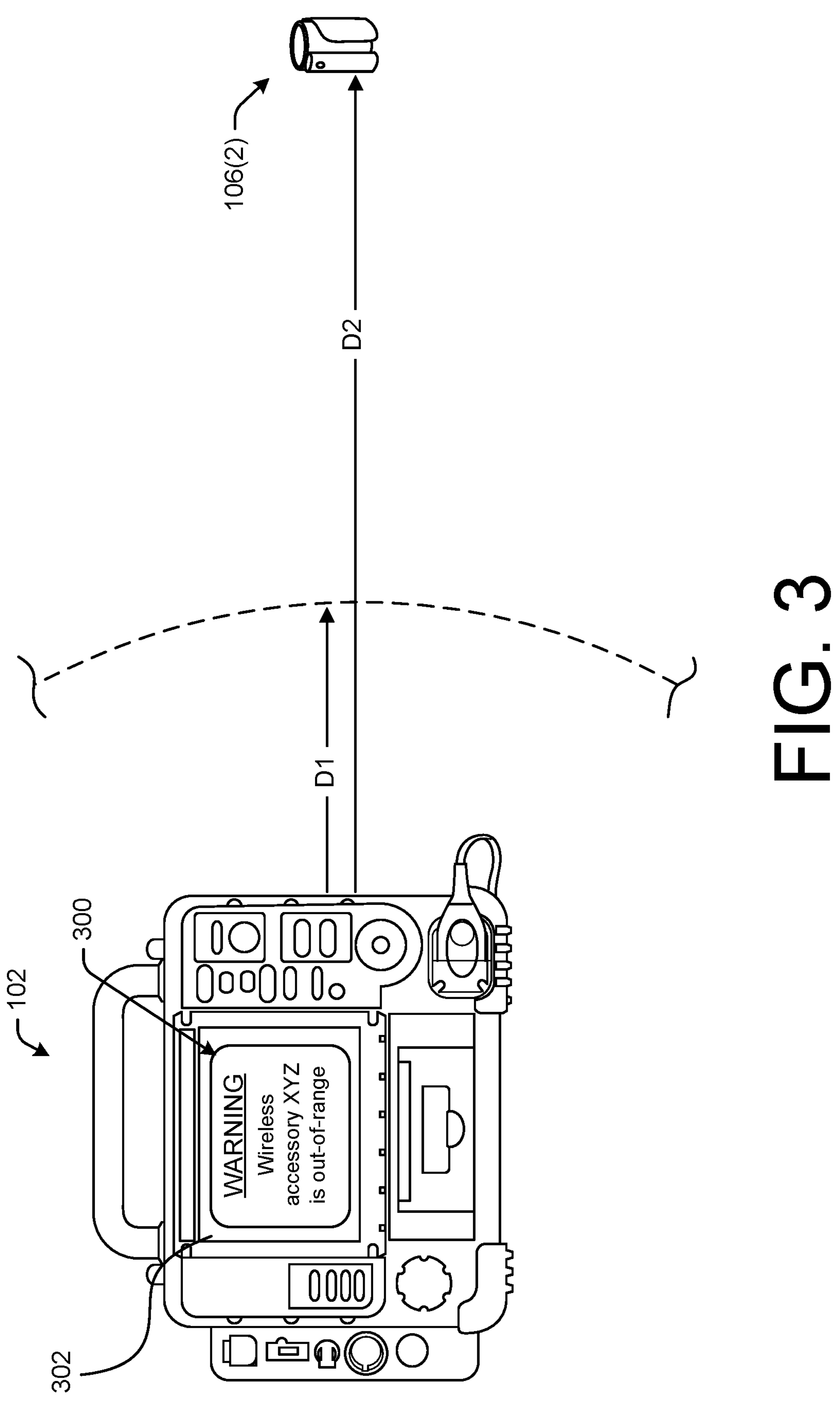
FIG. 3 illustrates an example medical device outputting a visual indication that a wireless accessory is out-of-range, according to the techniques described herein.

FIG. 3 illustrates an example medical device 102 outputting a visual indication 300 that a wireless accessory 106(2) is out-of-range, according to the techniques described herein. As mentioned above, in some examples, the accessory dock 104 functions as a tether for keeping track of wireless accessories 106 (e.g., tracking location and/or distance of the accessories 106 relative to the medical device 102 and/or the accessory dock 104). In the example of FIG. 3, the second wireless accessory 106(2), which was previously paired with the medical device 102, has moved to a location that is a distance, D2, from the medical device 102 that satisfies (e.g., is equal to or greater than, or is strictly greater than) a threshold distance, D1. This threshold distance, D1, is configurable and can be thought of as a geofence surrounding the medical device 102. In some examples, the threshold distance, D1, is about 10 meters, 15 meters, 20 meters, or the like. Accordingly, the processor(s) 128 of the medical device 102 may be configured to execute instructions (e.g., the wireless accessory module 134) stored in memory 130 to determine a distance between the medical device 102 and any given wireless accessory 106 that has been paired with the medical device 102, and to compare accessory's distance to the threshold distance, D1, to determine if the accessory 106 is out-of-range. This distance determination can be made using any suitable technology. In some examples, the medical device 102 is configured to send a signal or a packet to a particular wireless accessory 106 and the wireless accessory 106 is configured to send a signal or the packet back to the medical device 102 and the medical device 102 may measure a round trip time of this back-and-forth communication to calculate a distance of the wireless accessory 106 relative to the medical device 102. Other techniques for wireless accessory ranging include radio frequency (RF) signal strength or power (e.g., determining whether RF power associated with the wireless accessory 106 fails to satisfy a threshold power level), time-of-flight (ToF) techniques, using a location tracking component of the wireless accessory 106, such as a Global Positioning System (GPS) receiver of the wireless accessory 106 to determine a current location thereof, or the like. As illustrated in FIG. 3, if the distance, D2, between the medical device 102 and the wireless accessory 106(2) satisfies the threshold distance, D1, the processor(s) 128 of the medical device 102 may cause an output device (e.g., a display 302) of the medical device 102 to output the visual indication 300, which may indicate that the wireless accessory 106(2) is out-of-range. In some examples, the visual indication 300 may indicate that the wireless accessory 106(2) may have been lost. It is not uncommon for users of medical devices 102 to inadvertently leave an accessory at a scene where care was being provided to a subject. In these instances, the wireless tethering functionality described above may help avoid losing a wireless accessory 106 because a user may see the visual indication 300 and may search for the wireless accessory 106 before leaving an emergency scene, for example.

Figures 4, 5:
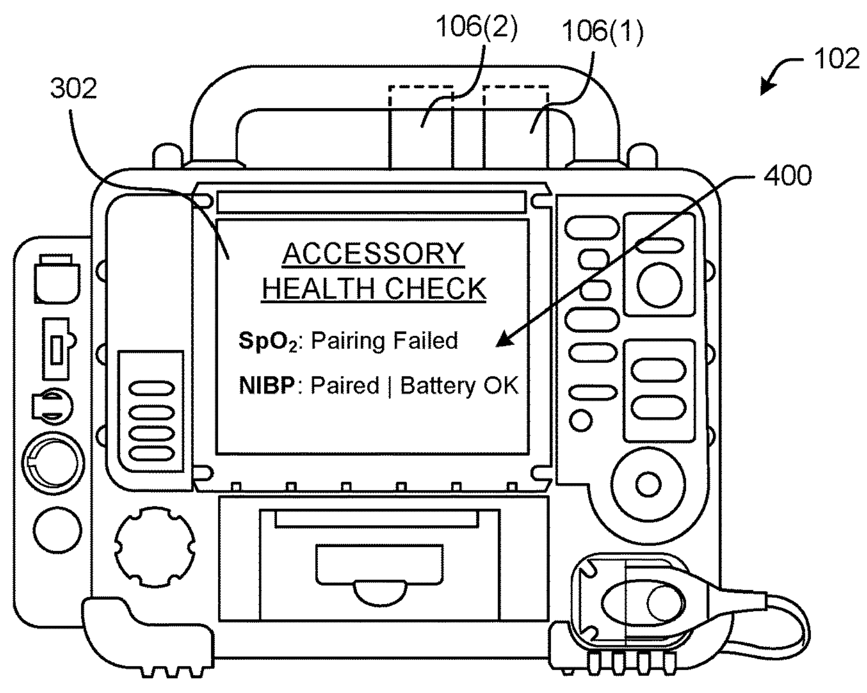
FIG. 4 an example medical device outputting a visual indication of wireless accessory readiness based on an accessory health check performed by the medical device, according to the techniques described herein.
FIG. 5 is a cross-sectional view of a docking receptacle of an accessory dock of a medical device, the docking receptacle having a wireless accessory retainer(s) to retain a wireless accessory within the docking receptacle, according to the techniques described herein.

FIG. 4 an example medical device 102 outputting a visual indication 400 of wireless accessory readiness based on an accessory health check performed by the medical device 102, according to the techniques described herein. In order to help ensure that the wireless accessories 106 are ready to be used with the medical device 102 as soon as a user undocks the accessories 106 from the accessory dock 104, the processor(s) 128 of the medical device 102 may be configured to execute instructions (e.g., the wireless accessory module 134) stored in memory 130 to perform an accessory health check. This accessory health check may determine, on an individual accessory 106 basis, whether the wireless accessory 106 is ready to be used with the medical device 102. For multiple wireless accessories, the accessory health check may be performed one-by-one for each wireless accessory 106, in some examples. The accessory health check can be triggered in various ways and may involve determining whether one or more criteria are met in order to make a "pass/fail" determination for a given wireless accessory 106.

In some examples, upon determining that a wireless accessory 106 has been docked in a docking receptacle 108, the processor(s) 128 of the medical device 102 may perform an accessory health check for that docked accessory 106. In some examples, docking an accessory 106 does not trigger the accessory health check by itself, and the accessory health check may be performed on the occurrence of a different trigger event. For example, the processor(s) 128 of the medical device 102 may be triggered to perform the accessory health check in response to the user powering on the medical device 102. In some examples, the performance of the accessory health check is part of, or performed immediately after, a boot sequence of the medical device 102. In some examples, the medical device 102 may be configured to wait a predefined period of time between performing sequential accessory health checks for the same wireless accessory 106. Accordingly, the trigger event for an accessory health check may be a lapse of the predefined period of time since a previous accessory health check as performed for the particular accessory 106. For example, accessory health checks may be performed in accordance with a schedule. In some examples, the medical device 102 may be configured to wait a predefined period of time after a wireless accessory 106 is docked in the accessory dock 104 before performing an accessory health check for that accessory 106, which may allow the accessory 106 enough time to recharge its battery 122 to a sufficient charge level that will result in passing the accessory health check.

Determining whether a wireless accessory 106 passes or fails an accessory health check, various criteria may be evaluated. For example, the processor(s) 128 of the medical device 102 may determine whether the wireless accessory 106 has been paired with the medical device to communicate wirelessly with the medical device 102. In this example, if the wireless accessory 106 was not paired with the medical device 102 (e.g., if a pairing procedure failed), the wireless accessory 106 may fail the accessory health check. This is illustrated in FIG. 4 via the visual indication 400, which indicates that the first wireless accessory 106(1) (e.g., $SpO_2$ sensor) is not ready to be used with the medical device 102 because a pairing procedure failed. In another example, the processor(s) 128 of the medical device 102 may determine whether a charge level of the battery 122 of a wireless accessory 106 satisfies (e.g., is equal to or greater than, or is strictly greater than) a threshold charge level (e.g., more than 50% of full charge). In this example, if the charge level of the battery 122 fails to satisfy a threshold charge level, the wireless accessory 106 may fail the accessory health check. In the example of FIG. 4, the second wireless accessory

106(2) (e.g., NIBP sensor) has passed the accessory health check, and the visual indication 400 indicates that it has passed by indicating that the accessory 106(2) is paired, and the battery is "OK", meaning that the charge level of the battery 122 of the wireless accessory 106(2) satisfies the threshold charge level. Other checks may be performed as part of the accessory health check, such as determining whether software and/or firmware of the accessory 106 is not outdated (e.g., the accessory 106 has the latest software and/or firmware installed thereon), checking other parameters, such as operability of component parts of the accessory 106. In some examples, these checks may be performed by the accessory 106 itself as a "self-diagnosis." In some examples, the medical device 102 is configured to send a "wakeup" signal to the accessory 106 that is to be checked for readiness so that the accessory health check can be performed while the accessory 106 is powered on (as opposed to being powered off or in a sleep/low-power state).

FIG. 5 is a cross-sectional view of a docking receptacle 108 of the accessory dock 104 of the medical device 102, the docking receptacle 108 having a wireless accessory retainer(s) 500(1), 500(2) to retain a wireless accessory 106 within the docking receptacle 108, according to the techniques described herein. The retainer(s) 500(1), 500(2) may be any suitable type of retainer. In the example of FIG. 5, the retainer(s) 500(1), 500(2) may represent magnets disposed at a bottom of the docking receptacle 108. These magnets 500(1), 500(2) are configured to exert an attractive force on magnets 502(1) and 502(2) of the wireless accessory 106, such as magnets disposed on a housing of the accessory 106 on a side that faces a bottom of the docking receptacle 108. Although multiple magnets are shown in FIG. 5, the docking receptacle 108 may include a single magnet, or more than two magnets to retain the wireless accessory 106 in the docking receptacle 108. In another example, the docking receptacle 108 may include a retainer(s) in the form of a detent(s). In these examples, the retainer(s), despite retaining the wireless accessory 106 in the docking receptacle 108, may also allow for removal of the wireless accessory 106 from the docking receptacle 108 upon an undocking force applied to the wireless accessory 106 that satisfies a threshold. Such a threshold may be greater than a typical force exerted on the wireless accessory 106 during typical transport of the medical device 102 with the wireless accessory 106 docked in the accessory dock 104, and less than a force that an average user can apply to the wireless accessory 106 to undock the accessory 106. In other words, the retainer(s) included in the docking receptacle 108, such as the retainer(s) 500(1), 500(2) in the form of magnets, may prevent the accessory 106 from falling out of the accessory dock 104 when the medical device 102 is being transported in an ambulance or carried by an EMT, for instance, yet the average user can easily undock the accessory 106 by pulling on the accessory 106 with a force that satisfies the above-mentioned threshold (e.g., a force that exceeds the attractive force of the magnets 500, 502 in the example of FIG. 5. The docking receptacle 108 may include other types of retainers for retaining the accessory 106 in the docking receptacle 108, such as a latch(es), a lock(s), a pin(s), etc. In some examples, the accessory dock 104 may include respective buttons next to each docking receptacle 108 that can be pressed by a user to release/unlock the accessory 106 that is retained by a latch or a lock.

The processes described herein represent sequences of operations that can be implemented in hardware, software, or a combination thereof. In the context of software, the blocks represent computer-executable instructions stored on one or more computer-readable storage media that, when executed by a processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes. In some examples, an operation(s) of the process may be omitted entirely. Moreover, the processes described herein can be combined in whole or in part with each other or with other processes.

Figure 6:
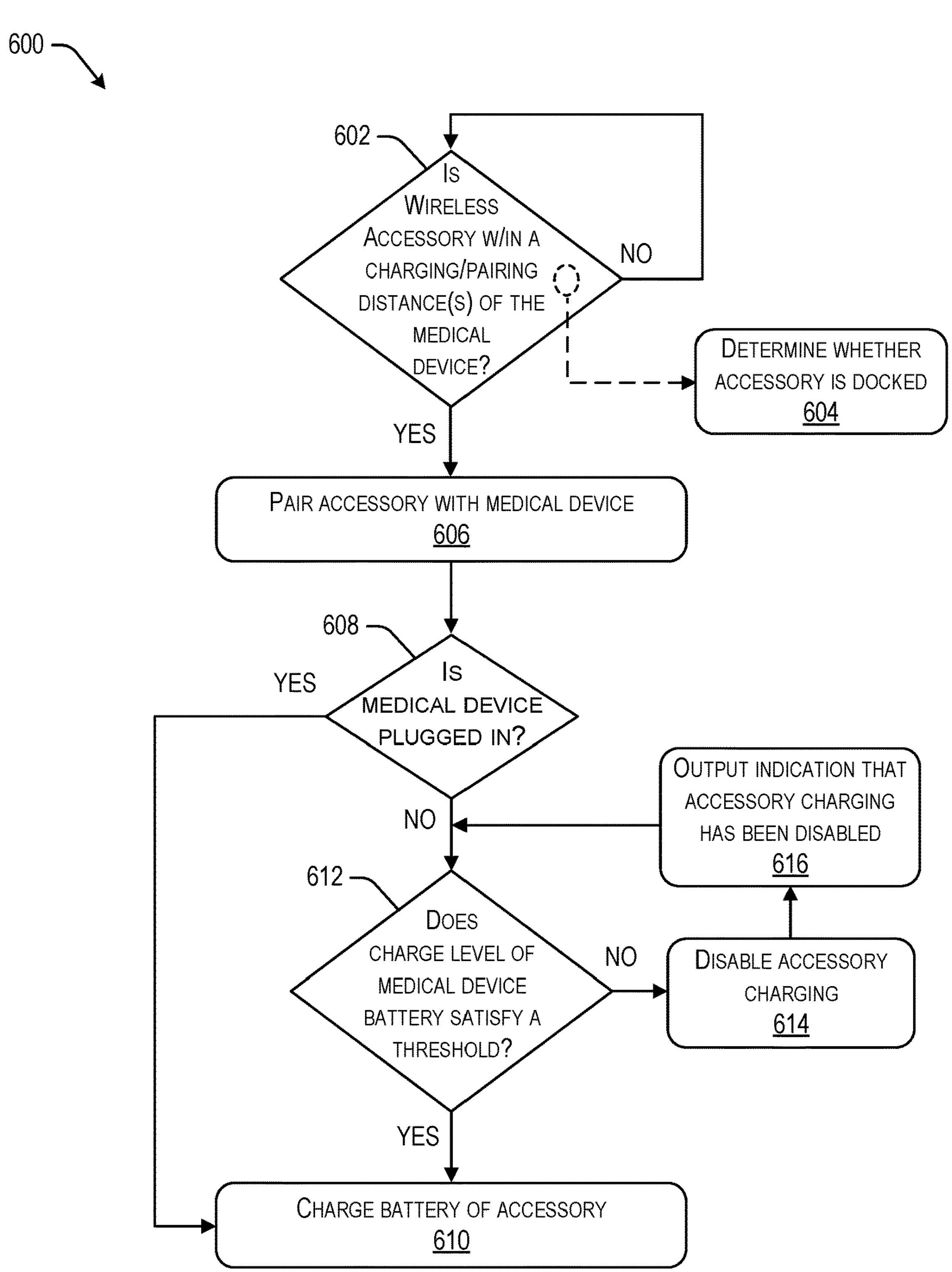
FIG. 6 illustrates an example process for pairing a wireless accessory with a medical device and for charging a battery of the wireless accessory, according to the techniques described herein.

FIG. 6 illustrates an example process 600 for pairing a wireless accessory 106 with a medical device 102 and for charging a battery 122 of the wireless accessory 106, according to the techniques described herein. For discussion purposes, the process 600 is described with reference to the previous figures.

At 602, a determination is made as to whether a wireless accessory 106 is positioned within a threshold distance(s) of a medical device 102. In some examples, the determination at block 602 may be made by a processor(s) 128 of the medical device 102, the medical device 102 having an accessory dock 104 with at least one docking receptacle 108 configured to receive the wireless accessory 106. In some examples, the medical device 102 is a monitor-defibrillator with an accessory dock 104. In some examples, the threshold distance evaluated at block 602 is a single threshold distance that corresponds to both a pairing distance and a wireless charging distance. In some examples, multiple different threshold distances may be evaluated at block 602, such as a first threshold distance associated with a wireless charging range/distance, and a second threshold distance associated with a pairing range/distance. In some examples, as indicated by block 604, the determination at block 602 involves determining whether the wireless accessory is docked in the docking receptacle 108 of the accessory dock 104, which inherently indicates that the accessory 106 is within the threshold distance(s) of the medical device 102 because the accessory 106 is contacting the medical device 102 when the accessory 106 is docked in the accessory dock 104 of the medical device 102.

In some examples, the determination is made at block 602 based on the charging technology and/or the pairing technology employed by the system 100. For example, the processor(s) 128 of the medical device 102 may determine that the wireless accessory 106 is within the threshold distance(s) at block 602 based on proximity of respective NFC chips in the devices 102, 106 (e.g., if a first NFC chip of the wireless accessory 106 is positioned within a threshold distance of a second NFC chip of the medical device 102). In this example, a second NFC chip of the medical device 102 may be disposed at the docking receptacle 108 where the accessory 106 is docked. In some examples, the processor(s) 128 of the medical device 102 may be configured to determine whether a first induction coil of the accessory 106 is within a threshold distance of, and/or aligned with, a second induction coil of the medical device 102. In these examples, the determination of whether the wireless accessory 106 is within charging and/or pairing range/distance of the medical device 102 can be made upon the wireless accessory 106 being docked in the docking receptacle 108. For example, the accessory dock 104, if made of a rigid, or semi-rigid, material (e.g., molded plastic), may orient the wireless accessory 106 in a particular orientation when the accessory 106 is docked in the docking receptacle 108 such that close proximity and alignment of NFC chips and/or induction coils in the respective devices 102, 106 is achieved upon the accessory 106 being docked in the docking receptacle 108.

If the accessory 106 is not within the threshold distance(s) of the medical device 102 at block 602 (e.g., if the accessory 106 is undocked), the process 600 follows the NO route to continue monitoring whether the accessory 106 is brought within the threshold distance(s) (e.g., monitoring for the accessory 106 being docked in the accessory dock 104). As soon as a wireless accessory 106 is within the threshold distance(s) (e.g., docked in the accessory dock 104) at block 602, the process 600 follows the YES route from block 602 to block 606.

At 606, the accessory 106 pairs with the medical device 102 upon being positioned within the threshold distance(s) of the medical device 102 (e.g., upon being docked in the docking receptacle 108). In some examples, pairing is implemented at block 606 using any suitable technology, such as NFC, a passive tag (e.g., a passive RFID tag), BLUETOOTH®, etc. In an illustrative example, the wireless accessory 106(1) pairs with the medical device 102 based on a first NFC chip of the wireless accessory 106 being positioned within the threshold distance of a second NFC chip of the medical device 102, such as a second NFC chip housed in the accessory dock 104 at a location of the docking receptacle 108. In this example, the threshold distance may be satisfied when the wireless accessory 106 is docked in the docking receptacle 108, as noted above, and/or when the accessory 106 is slightly farther away from the medical device 102, yet still within pairing range/distance thereof. In another example, the wireless accessory 106 pairs with the medical device 102 at block 606 based on a passive RFID tag of the wireless accessory 106 being detected by a RFID reader of the medical device 102.

In some examples, the medical device 102 and the wireless accessory 106 exchange pairing information at block 606, and this pairing information is usable by the medical device 102 and the wireless accessory 106 to communicate wirelessly (e.g., via respective transceivers 126, 132) after the wireless accessory 106 is undocked and/or after the wireless accessory 106 moves farther away from the medical device 102. For example, the devices 102, 106 may exchange BLUETOOTH® pairing information at block 606. In this manner, when the accessory 106 is undocked and moved farther away from the paired medical device 102, the accessory 106 knows that it should be talking to a particular medical device 102, and the medical device 102 knows that it should be talking to a particular accessory 106. Accordingly, the pairing at block 606 ensures that the wireless accessory 106 communicates wirelessly with the correct medical device 102, and that data (e.g., sensitive patient data) is sent to the correct medical device 102. In other words, the pairing of the wireless accessory 106 with the medical device 102 at block 606 provides a definitive and secure affirmation of the accessory 106 being paired with a medical device 102 with which it should communicate.

At 608, a determination can be made as to whether the medical device 102 is plugged in (e.g., connected to mains electricity). For example, a processor(s) 128 of the medical device 102 may determine, at block 608, whether a power cable is connected to a power connector 110 of the medical device 102 and to an external source of power (e.g., a power outlet with access to mains electricity, or grid power). If the processor(s) 128 of the medical device 102 determines that the medical device 102 is plugged in, the process 600 follows the YES route from block 608 to block 610.

At 610, the wireless accessory 106 receives power from the medical device 102 to recharge the battery 122 of the accessory 106 upon the accessory 106 being positioned within the threshold distance(s) of the medical device 102 (e.g., upon being docked in the docking receptacle 108). In some examples, the power is received wirelessly at block 610. For example, the wireless accessory 106 may include a first induction coil that recharges the battery 122 at block 610 in response to magnetic flux generated by a second induction coil of the medical device 102. It is to be appreciated, however, that the charging may be implemented in various ways at block 610, such as via radio charging, inductive charging (or near field charging), magnetic resonance charging, and/or electric field coupling. In some examples, the power is received at block 610 via a power connector of the accessory 106, which can be connected to a corresponding power connector (e.g., USB connector) in the docking receptacle 108, if the accessory 106 is docked in the docking receptacle 108. If the processor(s) 128 of the medical device 102 determines, at block 608, that the medical device 102 is not plugged in (e.g., that the medical device 102 does not have access to mains electricity), the process 600 follows the NO route from block 608 to block 612.

At 612, the processor(s) 128 of the medical device 102 determines whether a charge level of a battery 112(1), 112(2) of the medical device 102 satisfies (e.g., is equal to or greater than, or is strictly greater than) a threshold charge level. The threshold charge level evaluated at block 612 is configurable and may be set at a charge level that is adequate (or more than adequate) to carry out the primary function(s) of the medical device 102 for a period of time without access to mains electricity. For example, the threshold charge level may be set to a level that is sufficient to monitor and/or treat a patient at a rescue scene for a period of several hours, and/or a level that is sufficient to operate periodically throughout a day (e.g., a 12 hour period, or a 24 hour period). If the processor(s) 128 of the medical device 102 determines that the charge level of the battery 112(1), 112(2) of the medical device 102 satisfies the threshold charge level, the process 600 follows the YES route from block 612 to block 610, where the wireless accessory 106 receives power from the medical device 102 to recharge the battery 122 of the accessory 106, as described above. If the processor(s) 128 of the medical device 102 determines that the charge level of the battery 112(1), 112(2) of the medical device 102 fails to satisfy the threshold charge level, the process 600 follows the NO route from block 612 to block 614.

At 614, wireless accessory charging is disabled (e.g., by the processor(s) 128 of the medical device 102) based on the charge level of the battery 112(1), 112(2) of the medical device 102 failing to satisfy a threshold charge level. After the wireless accessory charging is disabled at block 614, the wireless accessory 106 is prevented from receiving power from the battery 112(1), 112(2) of the medical device 102 in order to reserve battery power for the primary function(s) of the medical device 102.

At 616, a visual indication that the wireless accessory charging has been disabled is output. For example, the example visual indication 206 and/or 208 may be output via a display 200 of the accessory 106, as shown in FIG. 2B. Additionally, or alternatively, a similar visual indication may be output via a display 302 of the medical device 102. Additionally, or alternatively, other types of output devices (e.g., output devices 124 of the accessory 106 and/or the medical device 102) may output indications that wireless accessory charging has been disabled, such as illuminating a red-colored LED on the wireless accessory 106, or the like. Following block 616, the process 600 may iteratively check the charge level of the battery 112(1), 112(2) of the medical device 102 at block 612 to determine if the charge level satisfies the threshold, and, if so, wireless accessory charging can be enabled and the battery 122 of the accessory 106 is charged at block 610.

Figure 7:
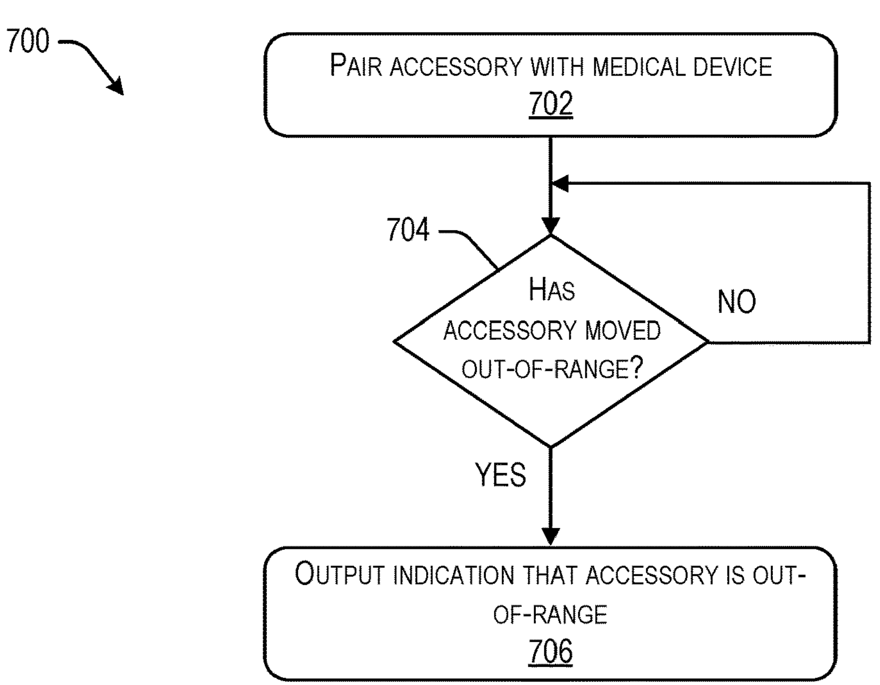
FIG. 7 illustrates an example process for notifying a user that a wireless accessory is out-of-range of a medical device, according to the techniques described herein.

FIG. 7 illustrates an example process 700 for notifying a user that a wireless accessory 106 is out-of-range of a medical device 102, according to the techniques described herein. For discussion purposes, the process 700 is described with reference to the previous figures.

At 702, an accessory 106 pairs with a medical device 102. The operations at block 702 may be similar to the operations described above with respect to block 606 of the process 600. For example, the accessory 106 may pair with the medical device 102 upon being positioned within a threshold distance of the medical device 102 (e.g., upon being docked in the docking receptacle 108).

At 704, a determination is made as to whether the accessory 106 has moved out-of-range of the medical device 102 (e.g., beyond a threshold distance from the medical device 102). In some examples, the processor(s) 128 of the medical device 102 makes the determination at block 704 by determining a distance between the medical device 102 and the wireless accessory 106 and comparing the distance to a threshold distance. For example, a tether functionality may be implemented for keeping track of wireless accessories 106 (e.g., tracking location and/or distance of the accessories 106 relative to the medical device 102 and/or the accessory dock 104), and a threshold distance, D1, (See FIG. 3) may be used as a geofence surrounding the medical device 102 to determine whether a distance between the medical device 102 and any given wireless accessory 106 has move out-of-range (e.g., to or beyond the geofence). This distance determination can be made using any suitable technology at block 704, such as by the medical device 102 sending a signal or a packet to the wireless accessory 106 and measuring a round trip time of a signal or packet returned from the wireless accessory 106. Other techniques for wireless accessory ranging that may be performed at block 704 include ToF techniques, using a location tracking component of the wireless accessory 106, such as a GPS receiver of the wireless accessory 106 to determine a current location thereof, or the like. If the processor(s) 128 of the medical device 102 determines that the distance between the medical device 102 and the wireless accessory 106 does not satisfy the threshold distance, D1, the process 700 follows the NO route from block 704 to continue monitoring the distance to the accessory 106 at block 704. If the processor(s) 128 of the medical device 102 determines that the distance between the medical device 102 and the wireless accessory 106 satisfies the threshold distance, D1, the process 700 follows the YES route from block 704 to block 706.

At 706, the processor(s) 128 of the medical device 102 causes an output device (e.g., a display 302) of the medical device 102 to output a visual indication 300 based on the distance satisfying the threshold distance, D1, which may be greater than a threshold distance used for pairing the accessory 106. The visual indication 300 output at block 706 may indicate that the wireless accessory 106 is out-of-range. In some examples, the visual indication 300 output at block 706 may indicate that the wireless accessory 106 may have been lost, which may motivate the user to search for the wireless accessory 106 before leaving an emergency scene, for example.

Figure 8:
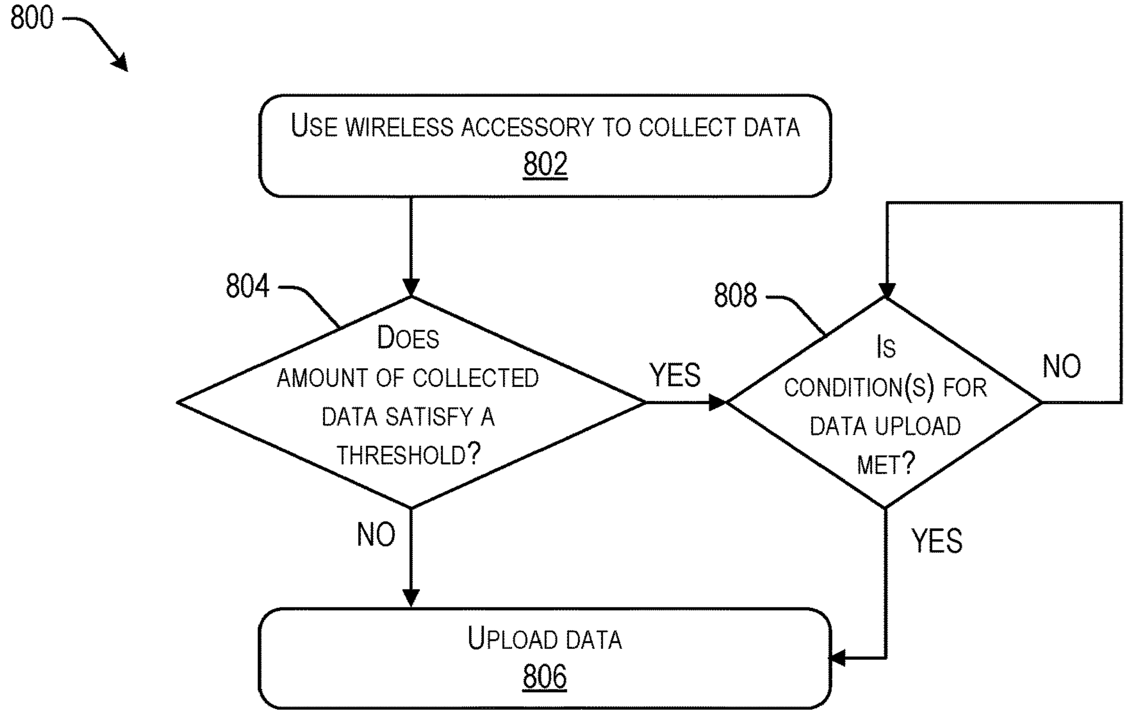
FIG. 8 illustrates an example process for determining when to upload data collected by a wireless accessory to a remote computing system, according to the techniques described herein.

FIG. 8 illustrates an example process 800 for determining when to upload data collected by a wireless accessory 106 to a remote computing system, according to the techniques described herein. For discussion purposes, the process 800 is described with reference to the previous figures.

At 802, a wireless accessory 106 is used to collect data. For example, the wireless accessory may be a wireless $SpO_2$ sensor, a wireless ECG detector, or wireless NIBP sensor, to name a few types of wireless medical accessories that might be used with a medical device 102, such as a monitor-defibrillator, at block 802. For example, an EMT may undock the wireless accessory 106 and attach the wireless accessory 106 to a subject experiencing sudden cardiac arrest to detect a physiological parameter of the subject, such as an oxygen saturation level of the subject, an ECG of the subject, and/or a blood pressure of the subject. Accordingly, data may be collected by the wireless accessory 106 during its use for detecting a physiological parameter of a subject at block 802. For example, such physiological parameter data (and possibly other data, such as timestamps, etc.) may be stored in the memory 118 of the wireless accessory 106.

At 804, a determination is made as to whether an amount of data collected by the wireless accessory 106 satisfies (e.g., is equal to or greater than, or is strictly greater than) a threshold amount of data. This determination may be made by a processor(s) 128 of the medical device 102, which is paired with the wireless accessory 106, and the amount of data can be determined/measured in any suitable manner, such as determining a number of bytes of data, megabytes of data, or the like. If the amount of data collected by the wireless accessory 106 fails to satisfy the threshold amount of data, the process 800 follows the NO route from block 804 to block 806 where the collected data is uploaded to a remote computing system. For example, the wireless accessory 106 may upload the data to a remote computing system (e.g., a server computer(s) in "the Cloud") over a wide area network, such as the Internet. In some examples, a transceiver 126 of the accessory 106 includes a cellular radio to upload collected data over a cellular network (e.g., via a nearby cell tower). In some examples, the medical device 102 and/or the accessory dock 104 of the medical device 102 functions as a hub to relay and/or route data received from the wireless accessory 106 to the remote computing system. In these examples, the wireless accessory 106 may transmit collected data to the medical device 102 and/or the accessory dock 104 via a short-range wireless protocol (e.g., BLUETOOTH®) and/or a local area network, and the medical device 102 or the accessory dock 104 utilizes a transceiver, such as a cellular radio, to upload the collected data over a cellular network (e.g., via a nearby cell tower). In some examples, a mobile wireless (e.g., Wi-Fi) hotspot of an ambulance may be utilized to upload the data at block 806. In any of these implementations, the wireless accessory 106 transmits the collected data to another device, whether that device is in the vicinity of the accessory 106 or remotely located from the accessory 106, and the accessory 106 may use the power of the battery 122 to transmit (e.g., upload) the data at block 806. Accordingly, if the process 800 follows the NO route from block 804 to block 806, the amount of data may be small enough to transmit (e.g., upload) without concern of depleting the battery 122 of the accessory 106 to do so.

At block 804, if the amount of data collected by the wireless accessory 106 satisfies the threshold amount of data, the process 800 follows the YES route from block 804 to block 808, where a determination is made as to whether one or more conditions are met for uploading the collected data. For example, the processor(s) 128 of the medical device 102 may determine, at block 808, whether the wireless accessory 106 is docked in a designated docking receptacle 108, and, hence, the battery 122 of the accessory 106 is recharging, as described herein. As another example, the processor(s) 128 of the medical device 102 may determine, at block 808, whether a charge level of the battery 122 of the accessory 106 satisfies a threshold charge level. In an illustrative example, the accessory 106 may have been used (wirelessly) over the course of a lengthy emergency rescue effort at block 802 where the accessory 106 collected a large amount of data and used up most of the battery 122 of the accessory 106 in doing so. In this example scenario, instead of immediately uploading the data and risking a full depletion of the battery 122 before the data upload is completed, the wireless accessory 106 may wait to transmit (e.g., upload) the collected data until the one or more criteria are met at block 808 (e.g., until the accessory 106 is at least docked and/or has enough battery power to proceed with the upload).

If the condition(s) is/are not met at block 808, the process 800 follows the NO route from block 808 to continue evaluating the condition(s). For example, it may take some time for a user to dock the wireless accessory 106 and/or for the charge level of the battery 122 of the accessory 106 to satisfy a threshold charge level, and while waiting for these conditions to be met, the process 800 may iterate the determination at block 808. In some examples, a prompt may be output on a display 200 of the accessory 106 and/or a display 302 of the medical device 102 that prompts the user to dock the accessory 106 in order to upload data that has been collected by the accessory 106. If the condition(s) is/are met at block 808, the process 800 follows the YES route from block 808 to block 806, where the collected data is uploaded, as described above.

Figure 9:
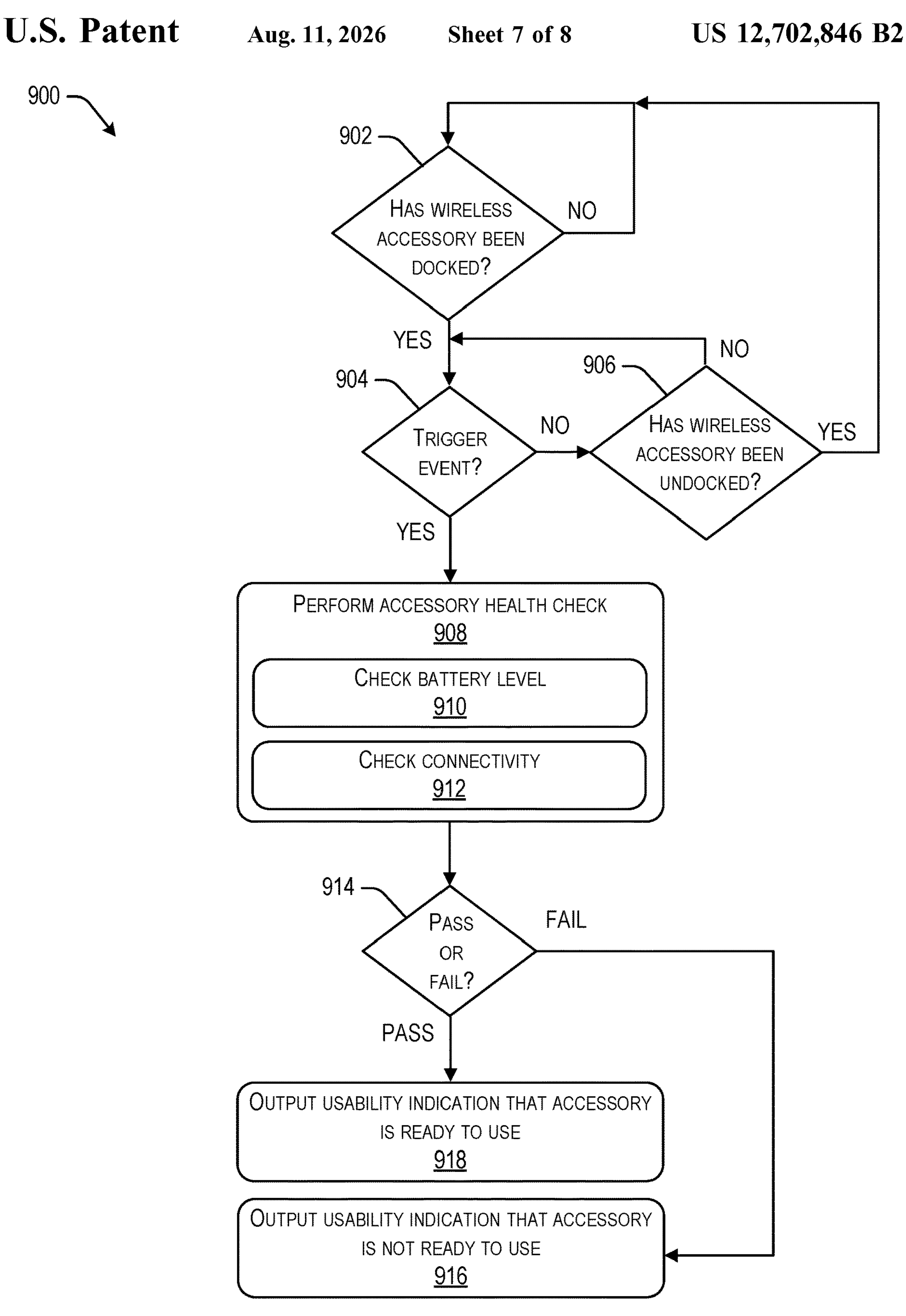
FIG. 9 illustrates an example process for performing an accessory health check to determine a readiness of a wireless accessory for use with a medical device, according to the techniques described herein.

FIG. 9 illustrates an example process 900 for performing an accessory health check to determine a readiness of a wireless accessory 106 for use with a medical device 102, according to the techniques described herein. For discussion purposes, the process 900 is described with reference to the previous figures.

At 902, a determination is made as to whether a wireless accessory 106 has been docked in a docking receptacle 108 of an accessory dock 104 of a medical device 102. In some examples, the determination is made at block 902 based on charging technology and/or pairing technology employed by the system 100. For example, a processor(s) 128 of the medical device 102 may determine that the wireless accessory 106 has been docked in a docking receptacle 108 at block 902 based on proximity of respective NFC chips in the devices 102, 106 (e.g., if a first NFC chip of the wireless accessory 106 is positioned within a threshold distance of a second NFC chip of the medical device 102). In this example, a second NFC chip of the medical device 102 may be disposed at the docking receptacle 108 where the accessory 106 is docked. In some examples, the processor(s) 128 of the medical device 102 may be configured to determine whether a first induction coil of the accessory 106 is within a threshold distance of, and/or aligned with, a second induction coil of the medical device 102. In these examples, the determination of whether the wireless accessory 106 is within charging and/or pairing range/distance of the medical device 102 can be made upon the wireless accessory 106 being docked in the docking receptacle 108. For example, the accessory dock 104, if made of a rigid, or semi-rigid, material (e.g., molded plastic), may orient the wireless accessory 106 in a particular orientation when the accessory 106 is docked in the docking receptacle 108 such that close proximity and alignment of NFC chips and/or induction coils in the respective devices 102, 106 is achieved upon the accessory 106 being docked in the docking receptacle 108.

If the processor(s) 128 of the medical device 102 determines that the wireless accessory 106 has not been docked in the docking receptacle 108 at block 902, the process 900 follows the NO route from block 902 to continue monitoring whether the accessory 106 is docked in the docking receptacle 108. If the processor(s) 128 of the medical device 102 determines that the wireless accessory 106 has been docked in the docking receptacle 108 at block 902, the process 900 follows the YES route from block 902 to block 904.

At 904, a determination is made as to whether a trigger event has occurred. For example, a processor(s) 128 of the medical device 102 may determine whether the trigger event has occurred at block 904 in various ways. In some examples, the trigger event occurs if the processor(s) 128 determines that the wireless accessory 106 has been docked. In other words, docking the wireless accessory 106 in the docking receptacle 108 may be the trigger event at block 904. As another example, the processor(s) 128 of the medical device 102 may determine, at block 904, whether a user has powered on the medical device 102 (e.g., by providing user input via an input device of the medical device 102). As yet another example, the processor(s) 128 of the medical device 102 may determine, at block 904, whether a predefined period of time has lapsed since the wireless accessory 106 was docked in the docking receptacle 108. This determination may be made using a clock or a timer that is started by the medical device 102 in response to determining that the accessory 106 has been docked. As yet another example, the processor(s) 128 of the medical device 102 may determine, at block 904, whether a predefined period of time has lapsed since a previous accessory health check was performed with respect to the wireless accessory 106 (or with respect to another wireless accessory 106).

If the processor(s) 128 of the medical device 102 determines that the trigger event has not occurred at block 904, the process 900 follows the NO route from block 904 to block 906, where a determination is made as to whether the wireless accessory 106 has been undocked from the docking receptacle 108. This determination at block 906 may be made in a similar manner to the determination at block 902, except in the reverse. For example, the processor(s) 128 of the medical device 102 may determine that the wireless accessory 106 has been undocked from the docking receptacle 108 at block 906 based on a lack of proximity between respective NFC chips in the devices 102, 106 (e.g., if a first NFC chip of the wireless accessory 106 is not positioned within a threshold distance of a second NFC chip of the medical device 102), and/or a lack of proximity and/or a lack of an alignment between a first induction coil of the accessory 106 and a second induction coil of the medical device 102. If the processor(s) 128 of the medical device 102 determines that the accessory 106 has not been undocked at block 906 (e.g., if the accessory 106 remains docked in the docking receptacle 108), the process 900 follows the NO route from block 906 to block 904 to continue monitoring for the occurrence of the trigger event. If the processor(s) 128 of the medical device 102 determines that the accessory 106 has been undocked at block 906 (e.g., if the accessory 106 is no longer docked in the docking receptacle 108), the process 900 follows the YES route from block 906 to block 902 to again monitoring whether the accessory 106 is docked in the docking receptacle 108.

If the processor(s) 128 of the medical device 102 determines that the trigger event has occurred at block 904, the process 900 follows the YES route from block 904 to block 908, where an accessory health check is performed to determine whether the wireless accessory 106 is ready to be used with the medical device 102. For example, the processor(s) 128 of the medical device 102 may cause the performance of the accessory health check at block 908, which may involve one or more health checks, as indicated by sub-blocks 910 and 912.

At 910, for example, the processor(s) 128 of the medical device 102 may determine a charge level of the battery 122 of the accessory 106. This may involve the wireless accessory 106 transmitting data (e.g., charge level data) to the medical device 102, the data indicative of the charge level of the battery 122. At 912, as another example, the processor(s) 128 of the medical device 102 may determine a pairing status of the accessory 106 and the medical device 102 (e.g., whether or not the wireless accessory 106 has been successfully paired with the medical device 102). Other checks may be performed at block 908 as part of the accessory health check, such as determining whether software and/or firmware of the accessory 106 is not outdated (e.g., the accessory 106 has the latest software and/or firmware installed thereon), checking other parameters, such as operability of component parts of the accessory 106. In some examples, these checks may be performed by the accessory 106 itself as a "self-diagnosis" and communicated to the medical device 102 at block 908. In some examples, the medical device 102 is configured to send a "wakeup" signal to the accessory 106 at block 908 so that the accessory health check can be performed while the accessory 106 is powered on (as opposed to being powered off or in a sleep/low-power state).

Following the performance of the accessory health check at block 908, a determination is made at block 914 as to whether the accessory 106 passed the health check or failed the health check. In some examples, this includes the processor(s) 128 of the medical device 102 determine whether a charge level of the battery 122 of the accessory 106 satisfies a threshold charge level, determining whether the wireless accessory 106 has been paired with the medical device 102 to communicate wirelessly with the medical device 102, and/or other determinations. In some examples, a score is computed based on various checks, such as by computing a weighted sum of sub-scores, and determining whether the score satisfies a threshold score. If the accessory 106 fails the health check, the process 900 follows the FAIL route from block 914 to block 916 where an output device (e.g., a display 302) of the medical device 102 outputs a visual indication that the wireless accessory 106 is not ready to be used with the medical device 102. An example of this indication 400 is shown in FIG. 4 with respect to the $SpO_2$ sensor that failed the pairing check. Accordingly, if the wireless accessory 106 is not ready to be used with the medical device 102 (e.g., because the accessory 106 failed the accessory health check), causing, by the processor(s) 128 of the medical device 102 may cause an output device (e.g., the display 302) to output an indication to the user to inform the user that the accessory 106 is not ready to be used so that the user can take corrective action (e.g., by ensuring that the battery 122 is recharged or replaced, by troubleshooting the connectivity of the accessory 106, etc.). If, on the other hand, the accessory 106 passes the health check, the process 900 follows the PASS route from block 914 to block 918 where an output device (e.g., a display 302) of the medical device 102 outputs a visual indication that the wireless accessory 106 is ready to be used with the medical device 102. An example of this indication 400 is shown in FIG. 4 with respect to the NIBP sensor that passed the accessory health check.

Figure 10:
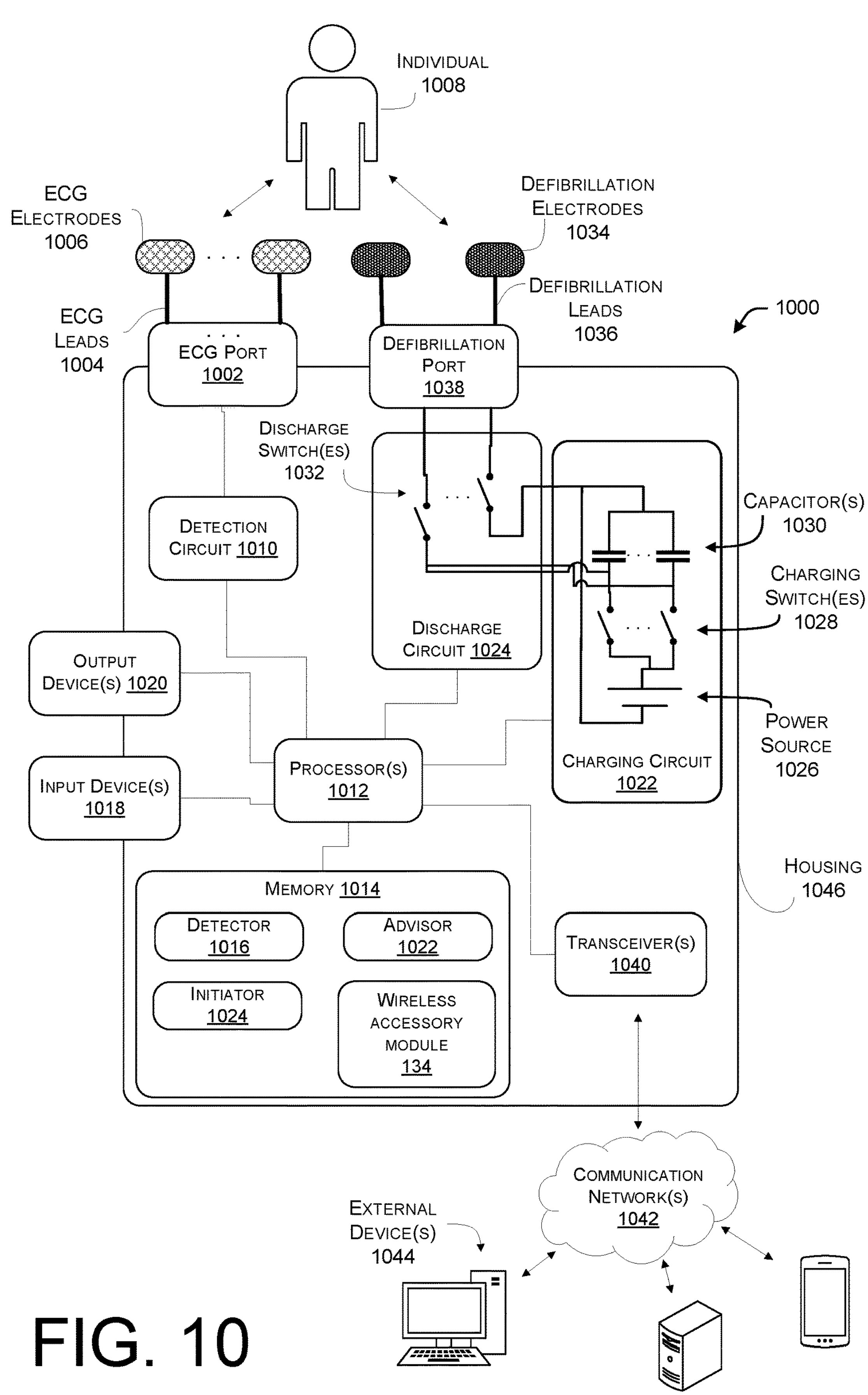
FIG. 10 illustrates an example of a monitor-defibrillator configured to perform various functions described herein.

FIG. 10 illustrates an example of an monitor-defibrillator 1000 (sometimes referred to herein as an "external defibrillator 1000") configured to perform various functions described herein. For example, the external defibrillator 1000 is the medical device 102 described above and introduced in FIG. 1.

The external defibrillator 1000 includes an electrocardiogram (ECG) port 1002 connected to multiple ECG leads 1004. In some cases, the ECG leads 1004 are removeable from the ECG port 1002. For instance, the ECG leads 1004 are plugged into the ECG port 1002. The ECG leads 1004 are connected to ECG electrodes 1006, respectively. In various implementations, the ECG electrodes 1006 are disposed on different locations on an individual 1008 (sometimes referred to herein as a "subject 1008", or a "patient 1008"). A detection circuit 1010 is configured to detect relative voltages between the ECG electrodes 1006. These voltages are indicative of the electrical activity of the heart of the individual 1008.

In various implementations, the ECG electrodes 1006 are in contact with the different locations on the skin of the individual 1008. In some examples, a first one of the ECG electrodes 1006 is placed on the skin between the heart and right arm of the individual 1008, a second one of the ECG electrodes 1006 is placed on the skin between the heart and left arm of the individual 1008, and a third one of the ECG electrodes 1006 is placed on the skin between the heart and a leg (either the left leg or the right leg) of the individual 1008. In these examples, the detection circuit 1010 is configured to measure the relative voltages between the first, second, and third ECG electrodes 1006. Respective pairings of the ECG electrodes 1006 are referred to as "leads," and the voltages between the pairs of ECG electrodes 1006 are known as "lead voltages." In some examples, more than three ECG electrodes 1006 are included, such that 5-lead or 12-lead ECG signals are detected by the detection circuit 1010.

The detection circuit 1010 includes at least one analog circuit, at least one digital circuit, or a combination thereof. The detection circuit 1010 receives the analog electrical signals from the ECG electrodes 1006, via the ECG port 1002 and the ECG leads 1004. In some cases, the detection circuit 1010 includes one or more analog filters configured to filter noise and/or artifact from the electrical signals. The detection circuit 1010 includes an analog-to-digital (ADC) in various examples. The detection circuit 1010 generates a digital signal indicative of the analog electrical signals from the ECG electrodes 1006. This digital signal can be referred to as an "ECG signal" or an "ECG."

In some cases, the detection circuit 1010 further detects an electrical impedance between at least one pair of the ECG electrodes 1006. For example, the detection circuit 1010 includes, or otherwise controls, a power source that applies a known voltage (or current) across a pair of the ECG electrodes 1006 and detects a resultant current (or voltage) between the pair of the ECG electrodes 1006. The impedance is generated based on the applied signal (voltage or current) and the resultant signal (current or voltage). In various cases, the impedance corresponds to respiration of the individual 1008, chest compressions performed on the individual 1008, and other physiological states of the individual 1008. In various examples, the detection circuit 1010 includes one or more analog filters configured to filter noise and/or artifact from the resultant signal. The detection circuit 1010 generates a digital signal indicative of the impedance using an ADC. This digital signal can be referred to as an "impedance signal" or an "impedance."

The detection circuit 1010 provides the ECG signal and/or the impedance signal one or more processors 1012 in the external defibrillator 1000. In some implementations, the processor(s) 1012 includes a central processing unit (CPU), a graphics processing unit (GPU), both CPU and GPU, or other processing unit or component known in the art. The processor(s) 1012 may represent the processor(s) 128 described above and introduced in FIG. 1.

The processor(s) 1012 is operably connected to memory 1014. The memory 1014 In various implementations, the memory 1014 may represent the memory 130 described above and introduced in FIG. 1. The memory 1014 is volatile (such as random access memory (RAM)), non-volatile (such as read only memory (ROM), flash memory, etc.) or some combination of the two. The memory 1014 stores instructions that, when executed by the processor(s) 1012, causes the processor(s) 1012 to perform various operations. In various examples, the memory 1014 stores methods, threads, processes, applications, objects, modules, any other sort of executable instruction, or a combination thereof. In some cases, the memory 1014 stores files, databases, or a combination thereof. In some examples, the memory 1014 includes, but is not limited to, RAM, ROM, electrically erasable programmable read-only memory (EEPROM), flash memory, or any other memory technology. In some examples, the memory 1014 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 1012 and/or the external defibrillator 1000. In some cases, the memory 1014 at least temporarily stores the ECG signal and/or the impedance signal.

In various examples, the memory 1014 includes a detector 1016, which causes the processor(s) 1012 to determine, based on the ECG signal and/or the impedance signal, whether the individual 1008 is exhibiting a particular heart rhythm. For instance, the processor(s) 1012 determines whether the individual 1008 is experiencing a shockable rhythm that is treatable by defibrillation. Examples of shockable rhythms include ventricular fibrillation (VF) and ventricular tachycardia (V-Tach). In some examples, the processor(s) 1012 determines whether any of a variety of different rhythms (e.g., asystole, sinus rhythm, atrial fibrillation (AF), etc.) are present in the ECG signal.

The processor(s) 1012 is operably connected to one or more input devices 1018 and one or more output devices 1020. Collectively, the input device(s) 1018 and the output device(s) 1020 function as an interface between a user and the defibrillator 1000. The input device(s) 1018 is configured to receive an input from a user and includes at least one of a keypad, a cursor control, a touch-sensitive display, a voice input device (e.g., a microphone), a haptic feedback device (e.g., a gyroscope), or any combination thereof. The output device(s) 1020 includes at least one of a display (e.g., the display 302 described above and introduced in FIG. 3), a speaker, a haptic output device, a printer, or any combination thereof. In various examples, the processor(s) 1012 causes a display among the output device(s) 1020 to visually output a waveform of the ECG signal and/or the impedance signal. In some implementations, the input device(s) 1018 includes one or more touch sensors, the output device(s) 1020 includes a display screen, and the touch sensor(s) are integrated with the display screen. Thus, in some cases, the external defibrillator 1000 includes a touchscreen configured to receive user input signal(s) and visually output physiological parameters, such as the ECG signal and/or the impedance signal.

In some examples, the memory 1014 includes an advisor 1022, which, when executed by the processor(s) 1012, causes the processor(s) 1012 to generate advice and/or control the output device(s) 1020 to output the advice to a user (e.g., a rescuer). In some examples, the processor(s) 1012 provides, or causes the output device(s) 1020 to provide, an instruction to perform CPR on the individual 1008. In some cases, the processor(s) 1012 evaluates, based on the ECG signal, the impedance signal, or other physiological parameters, CPR being performed on the individual 1008 and causes the output device(s) 1020 to provide feedback about the CPR in the instruction. According to some examples, the processor(s) 1012, upon identifying that a shockable rhythm is present in the ECG signal, causes the output device(s) 1020 to output an instruction and/or recommendation to administer a defibrillation shock to the individual 1008.

The memory 1014 also includes an initiator 1024 which, when executed by the processor(s) 1012, causes the processor(s) 1012 to control other elements of the external defibrillator 1000 in order to administer a defibrillation shock to the individual 1008. In some examples, the processor(s) 1012 executing the initiator 1024 selectively causes the administration of the defibrillation shock based on determining that the individual 1008 is exhibiting the shockable rhythm and/or based on an input from a user (received, e.g., by the input device(s) 1018). In some cases, the processor(s) 1012 causes the defibrillation shock to be output at a particular time, which is determined by the processor(s) 1012 based on the ECG signal and/or the impedance signal.

The processor(s) 1012 is operably connected to a charging circuit 1022 and a discharge circuit 1024. In various implementations, the charging circuit 1022 includes a power source 1026, one or more charging switches 1028, and one or more capacitors 1030. The power source 1026 includes, for instance, a battery. The power source 1026 may represent the battery 112(1) and/or the battery 112(2) described above and introduced in FIG. 1. The processor(s) 1012 initiates a defibrillation shock by causing the power source 1026 to charge at least one capacitor among the capacitor(s) 1030. For example, the processor(s) 1012 activates at least one of the charging switch(es) 1028 in the charging circuit 1022 to complete a first circuit connecting the power source 1026 and the capacitor to be charged. Then, the processor(s) 1012 causes the discharge circuit 1024 to discharge energy stored in the charged capacitor across a pair of defibrillation electrodes 1034, which are in contact with the individual 1008. For example, the processor(s) 1012 deactivates the charging switch(es) 1028 completing the first circuit between the capacitor(s) 1030 and the power source 1026, and activates one or more discharge switches 1032 completing a second circuit connecting the charged capacitor 1030 and at least a portion of the individual 1008 disposed between defibrillation electrodes 1034.

The energy is discharged from the defibrillation electrodes 1034 in the form of a defibrillation shock. For example, the defibrillation electrodes 1034 are connected to the skin of the individual 1008 and located at positions on different sides of the heart of the individual 1008, such that the defibrillation shock is applied across the heart of the individual 1008. The defibrillation shock, in various examples, depolarizes a significant number of heart cells in a short amount of time. The defibrillation shock, for example, interrupts the propagation of the shockable rhythm (e.g., VF or V-Tach) through the heart. In some examples, the defibrillation shock is 200 J or greater with a duration of about 0.015 seconds. In some cases, the defibrillation shock has a multiphasic (e.g., biphasic) waveform. The discharge switch(es) 1032 are controlled by the processor(s) 1012, for example. In various implementations, the defibrillation electrodes 1034 are connected to defibrillation leads 1036. The defibrillation leads 1036 are connected to a defibrillation port 1038, in implementations. According to various examples, the defibrillation leads 1036 are removable from the defibrillation port 1038. For example, the defibrillation leads 1036 are plugged into the defibrillation port 1038.

In various implementations, the processor(s) 1012 is operably connected to one or more transceivers 1040 that transmit and/or receive data over one or more communication networks 1042. For example, the transceiver(s) 1040 includes a network interface card (NIC), a network adapter, a local area network (LAN) adapter, or a physical, virtual, or logical address to connect to the various external devices and/or systems. In various examples, the transceiver(s) 1040 includes any sort of wireless transceivers capable of engaging in wireless communication (e.g., radio frequency (RF) communication). For example, the communication network(s) 1042 includes one or more wireless networks that include a $3^{rd}$ Generation Partnership Project (3GPP) network, such as a Long Term Evolution (LTE) radio access network (RAN) (e.g., over one or more LTE bands), a New Radio (NR) RAN (e.g., over one or more NR bands), or a combination thereof. In some cases, the transceiver(s) 1040 includes other wireless modems, such as a modem for engaging in WI-FI®, WIGIG®, WIMAX®, BLUETOOTH®, NFC, radio frequency identification (RFID), or infrared communication over the communication network(s) 1042. The transceiver(s) 1040 may represent the transceiver(s) 132 described above and introduced in FIG. 1.

The defibrillator 1000 is configured to transmit and/or receive data (e.g., ECG data, impedance data, data indicative of one or more detected heart rhythms of the individual 1008, data indicative of one or more defibrillation shocks administered to the individual 1008, etc.) with one or more external devices 1044 via the communication network(s) 1042. The external devices 1044 include, for instance, mobile devices (e.g., mobile phones, smart watches, etc.), Internet of Things (IOT) devices, medical devices, computers (e.g., laptop devices, servers, etc.), or any other type of computing device configured to communicate over the communication network(s) 1042. In some examples, the external device(s) 1044 is located remotely from the defibrillator 1000, such as at a remote clinical environment (e.g., a hospital). According to various implementations, the processor(s) 1012 causes the transceiver(s) 1040 to transmit data to the external device(s) 1044. In some cases, the transceiver(s) 1040 receives data from the external device(s) 1044 and the transceiver(s) 1040 provide the received data to the processor(s) 1012 for further analysis.

In some cases, the external device(s) 1044 include one or more of the wireless accessories 106 described above. According to various implementations, the memory 1014 further includes the wireless accessory module 134 described above and introduced in FIG. 1, which, when executed by the processor(s) 1012, causes the processor(s) 1012 to perform any of techniques, actions, and/or functions described herein, such as the processes 600, 700, 800, and/or 900 described herein.

In various implementations, the external defibrillator 1000 also includes a housing 1046 that at least partially encloses other elements of the external defibrillator 1000. For example, the housing 1046 encloses the detection circuit 1010, the processor(s) 1012, the memory 1014, the charging circuit 1022, the transceiver(s) 1040, or any combination thereof. In some cases, the input device(s) 1018 and output device(s) 1020 extend from an interior space at least partially surrounded by the housing 1046 through a wall of the housing 1046. In various examples, the housing 1046 acts as a barrier to moisture, electrical interference, and/or dust, thereby protecting various components in the external defibrillator 1000 from damage.

In some implementations, the external defibrillator 1000 is an automated external defibrillator (AED) operated by an untrained user (e.g., a bystander, layperson, etc.) and can be operated in an automatic mode. In automatic mode, the processor(s) 1012 automatically identifies a rhythm in the ECG signal, makes a decision whether to administer a defibrillation shock, charges the capacitor(s) 1030, discharges the capacitor(s) 1030, or any combination thereof. In some cases, the processor(s) 1012 controls the output device(s) 1020 to output (e.g., display 302) a simplified user interface to the untrained user. For example, the processor(s) 1012 refrains from causing the output device(s) 1020 to display a waveform of the ECG signal and/or the impedance signal to the untrained user, in order to simplify operation of the external defibrillator 1000.

In some examples, the external defibrillator 1000 is a monitor-defibrillator utilized by a trained user (e.g., a clinician, an emergency responder, etc.) and can be operated in a manual mode or the automatic mode. When the external defibrillator 1000 operates in manual mode, the processor(s) 1012 cause the output device(s) 1020 to display a variety of information that may be relevant to the trained user, such as waveforms indicating the ECG data and/or impedance data, notifications about detected heart rhythms, and the like.

EXAMPLE CLAUSES

1. A system comprising: a monitor-defibrillator comprising a power source and an accessory dock having docking receptacles configured to receive wireless accessories; and the wireless accessories, wherein individual ones of the wireless accessories comprise a battery and a transceiver and are configured to: docked in a docking receptacle of the docking receptacles; receive power from the power source upon being docked in the docking receptacle to automatically recharge the battery; automatically pair with the monitor-defibrillator upon being docked in the docking receptacle; and communicate wirelessly with the monitor-defibrillator via the transceiver in response to automatically pairing with the monitor-defibrillator.
2. The system of clause 1, wherein the wireless accessories comprise: a first wireless accessory configured to detect an oxygen saturation level of a subject; a second wireless accessory configured to detect an electrocardiogram (ECG) of the subject; and a third wireless accessory configured to detect a blood pressure of the subject.
3. The system of clause 2, wherein: a first docking receptacle of the docking receptacles has a first shape that matches a shape of a first housing of the first wireless accessory; a second docking receptacle of the docking receptacles has a second shape that matches a shape of a second housing of the second docking receptacle; a third docking receptacle of the docking receptacles has a third shape that matches a shape of a third housing of the third docking receptacle; and the first shape, the second shape, and the third shape are different shapes.

4. A system comprising: a medical device comprising an accessory dock having at least one docking receptacle configured to receive a wireless accessory; and the wireless accessory comprising a battery and a transceiver, wherein the wireless accessory is configured to: dock in the at least one docking receptacle; receive power from the medical device upon being positioned within a threshold distance of the medical device to charge the battery; and communicate wirelessly with the medical device via the transceiver.

5. The system of clause 4, wherein the power is received wirelessly.

6. The system of clause 4 or 5, wherein the power is received upon the wireless accessory being docked in the at least one docking receptacle.

7. The system of any one of clauses 4 to 6, wherein: the battery is a first battery; the medical device further comprises: a second battery; and a processor; the wireless accessory is configured to receive the power from the second battery to charge the first battery; the processor of the medical device is configured to: determine a charge level of the second battery; and disable wireless accessory charging based on the charge level failing to satisfy a threshold charge level; and the wireless accessory is prevented from receiving the power from the second battery after the wireless accessory charging is disabled.

8. The system of any one of clauses 4 to 7, wherein the medical device further comprises: a transceiver; and a processor configured to: determine an amount of data collected by the wireless accessory; and based on the amount of data satisfying a threshold amount of data, wait to upload the data to a remote computing system until at least one of: determining that the wireless accessory is docked in the at least one docking receptacle; or determining that a charge level of the battery satisfies a threshold charge level.

9. The system of any one of clauses 4 to 8, wherein the wireless accessory is further configured to: pair with the medical device upon being positioned within the threshold distance, or a different threshold distance, of the medical device; and communicate wirelessly with the medical device via the transceiver after pairing with the medical device.

10. The system of clause 9, wherein the wireless accessory is configured to pair with the medical device upon the wireless accessory being docked in the at least one docking receptacle.

11. A system comprising: a medical device comprising an accessory dock having at least one docking receptacle configured to receive a wireless accessory; and the wireless accessory comprising a transceiver, wherein the wireless accessory is configured to: dock in the at least one docking receptacle; pair with the medical device upon being positioned within a threshold distance of the medical device; and communicate wirelessly with the medical device via the transceiver after pairing with the medical device.

12. The system of clause 11, wherein wireless accessory is configured to pair with the medical device upon the wireless accessory being docked in the at least one docking receptacle.

13. The system of clause 11 or 12, wherein: pairing the wireless accessory with the medical device comprises the medical device and the wireless accessory exchanging pairing information; and wherein at least some of the pairing information is usable by the medical device and the wireless accessory to communicate wirelessly after the wireless accessory is undocked.

14. The system of any one of clauses 11 to 13, wherein the wireless accessory: further comprises a battery; and is further configured to receive power from the medical device upon being positioned within the threshold distance, or a different threshold distance, of the medical device to charge the battery.

15. The system of clause 14, wherein the power is received upon the wireless accessory being docked in the at least one docking receptacle.

16. The system of any one of clauses 11 to 15, wherein the threshold distance is a first threshold distance, and wherein the medical device further comprises: an output device; and a processor configured to: determine a distance between the medical device and the wireless accessory; and cause the output device to output a visual indication based on the distance satisfying a second threshold distance, wherein the second threshold distance is greater than the first threshold distance.

17. The system of any one of clauses 11 to 16, wherein the wireless accessory is configured to detect at least one of: an oxygen saturation level of a subject; an electrocardiogram (ECG) of the subject; a blood pressure of the subject; a carbon dioxide ($CO_2$) parameter associated with an airway of the subject; an airflow parameter associated with the airway of the subject; or a pressure parameter associated with the airway of the subject.

18. The system of any one of clauses 11 to 17, wherein: the wireless accessory is a first wireless accessory; the at least one docking receptacle is a first docking receptacle; the system further comprises a second wireless accessory; the accessory dock has multiple docking receptacles including the first docking receptacle and a second docking receptacle configured to receive the second wireless accessory; the first docking receptacle has a first shape that matches a shape of a first housing of the first wireless accessory; the second docking receptacle has a second shape that matches a shape of a second housing of the second docking receptacle; and the second shape is different than the first shape.

19. The system of any one of clauses 11 to 18, wherein the accessory dock is removably coupled to the medical device.

20. The system of any one of clauses 11 to 19, wherein the at least one docking receptacle includes a wireless accessory retainer to retain the wireless accessory within the at least one docking receptacle and to allow for removal of the wireless accessory from the at least one docking receptacle upon an undocking force applied to the wireless accessory that satisfies a threshold.

21. A system comprising: a monitor-defibrillator comprising a processor and an accessory dock having docking receptacles configured to receive wireless accessories; and the wireless accessories, wherein the processor is configured to: determine that a wireless accessory of the wireless accessories has been docked in a docking receptacle of the docking receptacle; and cause performance of an accessory health check to determine whether the wireless accessory is ready to be used with the monitor-defibrillator.

22. The system of clause 21, wherein: the processor is further configured to determine that a trigger event has occurred; and the processor is configured to cause performance of the accessory health check in response to determining that the trigger event has occurred.

23. The system of clause 22, wherein the trigger event comprises a user having powered on the monitor-defibrillator.

24. The system of clause 22 or 23, wherein the trigger event comprises the wireless accessory having been docked in the docking receptacle.

25. The system of any one of clauses 22 to 24, wherein the trigger event comprises a lapse of a predefined period of time since at least one of: the wireless accessory was docked in the docking receptacle; or a previous accessory health check was performed.

26. The system of any one of clauses 21 to 25, wherein: the wireless accessory comprise a battery and a transceiver; and causing performance of the accessory health check comprises: determining whether the wireless accessory has been paired with the monitor-defibrillator to communicate wirelessly with the monitor-defibrillator via the transceiver; and determining whether a charge level of the battery satisfies a threshold charge level.

27. A system comprising: a medical device comprising a processor and an accessory dock having at least one docking receptacle configured to receive a wireless accessory; and the wireless accessory, wherein the processor is configured to: determine that the wireless accessory has been docked in the at least one docking receptacle; and cause performance of an accessory health check to determine whether the wireless accessory is ready to be used with the medical device.

28. The system of clause 27, wherein: the processor is further configured to determine that a trigger event has occurred; and the processor is configured to cause performance of the accessory health check in response to determining that the trigger event has occurred.

29. The system of clause 28, wherein the trigger event comprises a user having powered on the medical device.

30. The system of clause 28 or 29, wherein the trigger event comprises the wireless accessory having been docked in the at least one docking receptacle.

31. The system of any one of clauses 28 to 30, wherein the trigger event comprises a lapse of a predefined period of time since at least one of: the wireless accessory was docked in the at least one docking receptacle; or a previous health check was performed.

32. The system of any one of clauses 27 to 31, wherein: the wireless accessory comprise a battery and a transceiver; and causing performance of the accessory health check comprises at least one of: determining whether the wireless accessory has been paired with the medical device to communicate wirelessly with the medical device via the transceiver; or determining whether a charge level of the battery satisfies a threshold charge level.

33. The system of any one of clauses 27 to 32, wherein the wireless accessory is configured to detect at least one of: an oxygen saturation level of a subject; an electrocardiogram (ECG) of the subject; a blood pressure of the subject; a carbon dioxide ($CO_2$) parameter associated with an airway of the subject; an airflow parameter associated with the airway of the subject; or a pressure parameter associated with the airway of the subject.

34. The system of any one of clauses 27 to 33, wherein: the wireless accessory is a first wireless accessory; the at least one docking receptacle is a first docking receptacle; the system further comprises a second wireless accessory; the accessory dock has multiple docking receptacles including the first docking receptacle and a second docking receptacle configured to receive the second wireless accessory; and the processor is further configured to: determine that the second wireless accessory has been docked in the second docking receptacle; and cause performance of the accessory health check to determine whether the second wireless accessory is ready to be used with the medical device.

35. A method comprising: determining, by a processor of a medical device, that a wireless accessory has been docked in a docking receptacle of an accessory dock of the medical device; and in response to determining that the wireless accessory has been docked in the docking receptacle, causing, by the processor, performance of an accessory health check to determine whether the wireless accessory is ready to be used with the medical device.

36. The method of clause 35, further comprising, in response to determining that the wireless accessory is not ready to be used with the medical device, causing, by the processor, an output device of the medical device to output a visual indication that the wireless accessory is not ready to be used with the medical device.

37. The method of clause 36, wherein: the wireless accessory comprise a battery and a transceiver; and the determining that the wireless accessory is not ready to be used with the medical device comprises at least one of: determining that the wireless accessory has not been paired with the medical device; or determining that a charge level of the battery fails to satisfy a threshold charge level.

38. The method of any one of clauses 35 to 37, further comprising: determining, by the processor, that a trigger event has occurred, wherein the causing of the performance of the accessory health check is in response to determining that the trigger event has occurred.

39. The method of clause 38, wherein the determining that the trigger event has occurred comprises determining that the medical device has been powered on.

40. The method of clause 38 or 39, wherein the determining that the trigger event has occurred comprises determining that a predefined period of time has lapsed since at least one of: the wireless accessory was docked in the docking receptacle; or a previous health check was performed.

While the example clauses described above are described with respect to one particular implementation, it should be understood that, in the context of this document, the content of the example clauses can also be implemented via a method, device, system, computer-readable medium, and/or another implementation. Additionally, any one of examples 1-40 may be implemented alone or in combination with any other of the examples 1-40.

CONCLUSION

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A system comprising:

a monitor-defibrillator comprising a power source and an accessory dock having docking receptacles configured to receive wireless accessories; and the wireless accessories, wherein individual ones of the wireless accessories comprise a battery and a transceiver and are configured to:

dock in a docking receptacle of the docking receptacles;

receive power from the power source upon being docked in the docking receptacle to automatically recharge the battery;

automatically pair with the monitor-defibrillator upon being docked in the docking receptacle; and communicate wirelessly with the monitor-defibrillator via the transceiver in response to automatically pairing with the monitor-defibrillator, wherein the monitor-defibrillator further comprises a processor configured to:

determine an amount of data collected by a wireless accessory of the wireless accessories; and based on the amount of the data satisfying a threshold amount of the data, wait to upload the data to a remote computing system until at least one of:

determining that the wireless accessory is docked in the docking receptacle; or determining that a charge level of the battery satisfies a threshold charge level.

2. The system of claim 1, wherein the wireless accessories comprise:

a first wireless accessory configured to detect an oxygen saturation level of a subject;

a second wireless accessory configured to detect an electrocardiogram (ECG) of the subject; and a third wireless accessory configured to detect a blood pressure of the subject.

3. The system of claim 2, wherein:

a first docking receptacle of the docking receptacles has a first shape that matches a shape of a first housing of the first wireless accessory;

a second docking receptacle of the docking receptacles has a second shape that matches a shape of a second housing of the second docking receptacle;

a third docking receptacle of the docking receptacles has a third shape that matches a shape of a third housing of the third docking receptacle; and the first shape, the second shape, and the third shape are different shapes.

4. A system comprising:

a medical device comprising an accessory dock having at least one docking receptacle configured to receive a wireless accessory; and the wireless accessory comprising a battery and a transceiver, wherein the wireless accessory is configured to:

dock in the at least one docking receptacle;

receive power from the medical device upon being positioned within a threshold distance of the medical device to charge the battery; and communicate wirelessly with the medical device via the transceiver, wherein the medical device further comprises a processor configured to:

determine an amount of data collected by the wireless accessory; and based on the amount of the data satisfying a threshold amount of the data, wait to upload the data to a remote computing system until at least one of:

determining that the wireless accessory is docked in the at least one docking receptacle; or determining that a charge level of the battery satisfies a threshold charge level.

5. The system of claim 4, wherein the power is received wirelessly.

6. The system of claim 4, wherein the power is received upon the wireless accessory being docked in the at least one docking receptacle.

7. The system of claim 4, wherein:

the battery is a first battery;

the medical device further comprises a second battery;

the wireless accessory is configured to receive the power from the second battery to charge the first battery;

the processor is further configured to:

determine a charge level of the second battery; and disable wireless accessory charging based on the charge level of the second battery failing to satisfy a second threshold charge level; and the wireless accessory is prevented from receiving the power from the second battery after the wireless accessory charging is disabled.

8. The system of claim 4, wherein the wireless accessory is further configured to:

pair with the medical device upon being positioned within the threshold distance, or a different threshold distance, of the medical device; and communicate wirelessly with the medical device via the transceiver after pairing with the medical device.

9. The system of claim 8, wherein the wireless accessory is configured to pair with the medical device upon the wireless accessory being docked in the at least one docking receptacle.

10. The system of claim 4, wherein:

the wireless accessory further comprises a first display;

the medical device further comprises a second display; and the processor is further configured to cause a prompt to be displayed on the first display or on the second display that prompts a user to dock the wireless accessory in order to upload the data.

11. A system comprising:

a medical device comprising an accessory dock having at least one docking receptacle configured to receive a wireless accessory; and the wireless accessory comprising a battery and a transceiver, wherein the wireless accessory is configured to:

dock in the at least one docking receptacle;

pair with the medical device upon being positioned within a threshold distance of the medical device; and communicate wirelessly with the medical device via the transceiver after pairing with the medical device, wherein the medical device further comprises a processor configured to:

determine an amount of data collected by the wireless accessory; and based on the amount of the data satisfying a threshold amount of the data, wait to upload the data to a remote computing system until at least one of:

determining that the wireless accessory is docked in the at least one docking receptacle; or determining that a charge level of the battery satisfies a threshold charge level.

12. The system of claim 11, wherein the wireless accessory is configured to pair with the medical device upon the wireless accessory being docked in the at least one docking receptacle.

13. The system of claim 11, wherein:

pairing the wireless accessory with the medical device comprises the medical device and the wireless accessory exchanging pairing information; and at least some of the pairing information is usable by the medical device and the wireless accessory to communicate wirelessly after the wireless accessory is undocked.

14. The system of claim 11, wherein the wireless accessory is further configured to receive power from the medical device upon being positioned within the threshold distance, or a different threshold distance, of the medical device to charge the battery.

15. The system of claim 14, wherein the power is received upon the wireless accessory being docked in the at least one docking receptacle.

16. The system of claim 11, wherein:

the threshold distance is a first threshold distance;

the medical device further comprises an output device; and the processor is further configured to:

determine a distance between the medical device and the wireless accessory; and cause the output device to output a visual indication based on the distance satisfying a second threshold distance, wherein the second threshold distance is greater than the first threshold distance.

17. The system of claim 11, wherein the wireless accessory is configured to detect at least one of:

an oxygen saturation level of a subject;

an electrocardiogram (ECG) of the subject;

a blood pressure of the subject;

a carbon dioxide ($CO_2$) parameter associated with an airway of the subject;

an airflow parameter associated with the airway of the subject; or a pressure parameter associated with the airway of the subject.

18. The system of claim 11, wherein:

the wireless accessory is a first wireless accessory;

the at least one docking receptacle is a first docking receptacle;

the system further comprises a second wireless accessory;

the accessory dock has multiple docking receptacles including the first docking receptacle and a second docking receptacle configured to receive the second wireless accessory;

the first docking receptacle has a first shape that matches a shape of a first housing of the first wireless accessory;

the second docking receptacle has a second shape that matches a shape of a second housing of the second docking receptacle; and the second shape is different than the first shape.

19. The system of claim 11, wherein the accessory dock is removably coupled to the medical device.

20. The system of claim 11, wherein the at least one docking receptacle includes a wireless accessory retainer to retain the wireless accessory within the at least one docking receptacle and to allow for removal of the wireless accessory from the at least one docking receptacle upon an undocking force applied to the wireless accessory that satisfies a threshold.

* * * * *